United States Patent
Bremel et al.

(10) Patent No.: US 7,138,562 B2
(45) Date of Patent: *Nov. 21, 2006

(54) TRANSGENIC ANIMALS

(75) Inventors: Robert D. Bremel, Hillpoint, WI (US); Anthony W. S. Chan, Aloha, OR (US); Jane C. Burns, LaJolla, CA (US)

(73) Assignee: Wisconsin Alumni research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/907,859

(22) Filed: Jul. 18, 2001

(65) Prior Publication Data

US 2002/0129393 A1   Sep. 12, 2002

Related U.S. Application Data

(63) Continuation of application No. 09/329,749, filed on Jun. 10, 1999, now Pat. No. 6,291,740, which is a continuation-in-part of application No. 08/821,984, filed on Mar. 19, 1997, now Pat. No. 6,080,912.

(51) Int. Cl.
*C12N 15/00* (2006.01)
*A01K 67/00* (2006.01)
*A01K 67/033* (2006.01)

(52) U.S. Cl. .............................. 800/23; 800/8; 800/14; 800/21

(58) Field of Classification Search .................. 800/14, 800/25, 21, 23, 8; 435/455, 325, 320.1
See application file for complete search history.

(56) References Cited

FOREIGN PATENT DOCUMENTS

WO     WO 90/08832     *   8/1990

OTHER PUBLICATIONS

Haskell et.al.; Efficient Production of Transgenic Cattle by Retroviral Infection of Early Embryos, 1995, Molecular Reproduction and Deveiopment 40: 386-390.*
Yee et.al.; Generation of High-Titer Pseudottped Retroviral Vectors with Very Broad Host Range, 1994, Methods In Cell Biology, vol. 43: 99-112.*
Friedrich, G., et al., "Promoter traps in embryonic stem cells: a genetic screen to identify and mutate developmental genes in mice," Genes and Development 5:1513-1523 (1991).
Lock, L.F., et al., "Studies of the mechanism of spontaneous germline ecotropic provirus acquisition in mice," The EMBO Journal 7:4169-4177 (1988).

* cited by examiner

*Primary Examiner*—Anne-Marie Falk
*Assistant Examiner*—Thaian N. Ton
(74) *Attorney, Agent, or Firm*—Quarles & Brady LLP

(57) ABSTRACT

The present invention provides improved methods and compositions for the generation of transgenic non-human animals. The present invention permits the introduction of exogenous nucleic acid sequences into the genome of unfertilized eggs (e.g., pre-maturation oocytes and pre-fertilization oocytes) by microinjection of infectious retrovirus into the perivitelline space of the egg. The methods of the present invention provide an increased efficiency of production of transgenic animals with a reduced rate of generating animals which are mosaic for the presence of the transgene.

21 Claims, 4 Drawing Sheets

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear -continued

```
    (ii) MOLECULE TYPE: other nucleic acid
         (A) DESCRIPTION: /desc = "DNA"

(xi) SEQUENCE DESCRIPTION: SEQ ID NO: 1:

GCATTGCATC AGCCATGATG                                              20

(2) INFORMATION FOR SEQ ID NO: 2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 2:

GATGGATTGC ACGCAGGTTC                                              20

(2) INFORMATION FOR SEQ ID NO: 3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 3:

GGCTATCGCT GGATGTGTCT                                              20

(2) INFORMATION FOR SEQ ID NO: 4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO: 4:

ACTGAACAAA TGGCACTAGT                                              20

(2) INFORMATION FOR SEQ ID NO: 5:

(i) SEQUENCE CHARACTERISTICS:
         (A) LENGTH: 1590 base pairs
         (B) TYPE: nucleic acid
         (C) STRANDEDNESS: double
         (D) TOPOLOGY: linear (ii) MOLECULE TYPE: other nucleic acid
         (A) DESCRIPTION: /desc = "DNA"

(ix) FEATURE:
         (A) NAME/KEY: CDS
         (B) LOCATION: 1..1587

(xi) SEQUENCE DESCRIPTION: SEQ ID NO: 5:

ATG GAT CTC TTT CCC ATT TTG GTC GTG GTG CTC ATG ACA GAT ACT GTC   48
Met Asp Leu Phe Pro Ile Leu Val Val Val Leu Met Thr Asp Thr Val
 1               5                  10                  15
```

-continued

| | |
|---|---|
| TTA GGG AAG TTT CAA ATT GTC TTC CCG GAT CAG AAT GAA CTG GAG TGG<br>Leu Gly Lys Phe Gln Ile Val Phe Pro Asp Gln Asn Glu Leu Glu Trp<br>    20              25              30 | 96 |
| AGA CCA GTT GTG GGT GAC TCT CGG CAT TGC CCA CAG TCA TCA GAA ATG<br>Arg Pro Val Val Gly Asp Ser Arg His Cys Pro Gln Ser Ser Glu Met<br>        35              40              45 | 144 |
| CAA TTC GAT GGA AGC AGA TCC CAG ACC ATA CTG ACT GGG AAA GCT CCC<br>Gln Phe Asp Gly Ser Arg Ser Gln Thr Ile Leu Thr Gly Lys Ala Pro<br>50              55              60 | 192 |
| GTG GGG ATC ACG CCC TCT AAA TCA GAT GGA TTT ATC TGC CAT GCC GCA<br>Val Gly Ile Thr Pro Ser Lys Ser Asp Gly Phe Ile Cys His Ala Ala<br>65              70              75              80 | 240 |
| AAA TGG GTG ACA ACA TGT GAT TTC AGG TGG TAT GGG CCG AAA TAC ATC<br>Lys Trp Val Thr Thr Cys Asp Phe Arg Trp Tyr Gly Pro Lys Tyr Ile<br>                85              90              95 | 288 |
| ACT CAT TCA ATA CAT CAT CTG AGA CCG ACA ACA TCA GAC TGT GAG ACA<br>Thr His Ser Ile His His Leu Arg Pro Thr Thr Ser Asp Cys Glu Thr<br>        100             105             110 | 336 |
| GCT CTC CAA AGG TAT AAA GAT GGG AGC TTA ATC AAT CTT GGA TTC CCC<br>Ala Leu Gln Arg Tyr Lys Asp Gly Ser Leu Ile Asn Leu Gly Phe Pro<br>115             120             125 | 384 |
| CCA GAA TCC TGC GGT TAT GCA ACA GTC ACA GAT TCT GAG GCA ATG TTG<br>Pro Glu Ser Cys Gly Tyr Ala Thr Val Thr Asp Ser Glu Ala Met Leu<br>130             135             140 | 432 |
| GTC CAA GTG ACT CCC CAC CAC GTT GGG GTG GAT GAT TAT AGA GGT CAC<br>Val Gln Val Thr Pro His His Val Gly Val Asp Asp Tyr Arg Gly His<br>145             150             155             160 | 480 |
| TGG ATC GAC CCA CTA TTT CCA GGA GGA GAA TGC TCC ACC AAT TTT TGT<br>Trp Ile Asp Pro Leu Phe Pro Gly Gly Glu Cys Ser Thr Asn Phe Cys<br>                165             170             175 | 528 |
| GAT ACA GTC CAC AAT TCA TCG GTG TGG ATC CCC AAG AGT CAA AAG ACT<br>Asp Thr Val His Asn Ser Ser Val Trp Ile Pro Lys Ser Gln Lys Thr<br>        180             185             190 | 576 |
| GAC ATC TGT GCC CAG TCT TTC AAA AAT ATC AAG ATG ACC GCA TCT TAC<br>Asp Ile Cys Ala Gln Ser Phe Lys Asn Ile Lys Met Thr Ala Ser Tyr<br>195             200             205 | 624 |
| CCC TCA GAA GGA GCA TTG GTG AGT GAC AGA TTT GCC TTC CAC AGT GCA<br>Pro Ser Glu Gly Ala Leu Val Ser Asp Arg Phe Ala Phe His Ser Ala<br>210             215             220 | 672 |
| TAT CAT CCA AAT ATG CCG GGG TCA ACT GTT TGC ATA ATG GAC TTT TGC<br>Tyr His Pro Asn Met Pro Gly Ser Thr Val Cys Ile Met Asp Phe Cys<br>225             230             235             240 | 720 |
| GAA CAA AAG GGG TTG AGA TTC ACA AAT GGA GAG TGG ATG GGT CTC AAT<br>Glu Gln Lys Gly Leu Arg Phe Thr Asn Gly Glu Trp Met Gly Leu Asn<br>                245             250             255 | 768 |
| GTG GAG CAA TCC ATC CGA GAG AAG AAG ATA AGT GCC ATC TTC CCA AAT<br>Val Glu Gln Ser Ile Arg Glu Lys Lys Ile Ser Ala Ile Phe Pro Asn<br>        260             265             270 | 816 |
| TGT GTT GCA GGG ACT GAA ATC CGA GCC ACA CTA GAA TCA GAA GGG GCA<br>Cys Val Ala Gly Thr Glu Ile Arg Ala Thr Leu Glu Ser Glu Gly Ala<br>275             280             285 | 864 |
| AGA ACT TTG ACG TGG GAG ACT CAA AGA ATG CTA GAT TAC TCT TTG TGT<br>Arg Thr Leu Thr Trp Glu Thr Gln Arg Met Leu Asp Tyr Ser Leu Cys<br>290             295             300 | 912 |
| CAG AAC ACC TGG GAC AAA GTT TCC AGG AAA GAA CCT CTC AGT CCG CTT<br>Gln Asn Thr Trp Asp Lys Val Ser Arg Lys Glu Pro Leu Ser Pro Leu<br>305             310             315             320 | 960 |
| GAC TTG AGC TAT CTG TCA CCA AGG GCT CCA GGG AAA GGC ATG GCC TAT<br>Asp Leu Ser Tyr Leu Ser Pro Arg Ala Pro Gly Lys Gly Met Ala Tyr<br>                325             330             335 | 1008 |

```
ACC GTC ATA AAC GGA ACC CTG CAT TCG GCT CAT GCT AAA TAC ATT AGA    1056
Thr Val Ile Asn Gly Thr Leu His Ser Ala His Ala Lys Tyr Ile Arg
            340                 345                 350

ACC TGG ATT GAT TAT GGA GAA ATG AAG GAA ATT AAA GGT GGA CGT GGA    1104
Thr Trp Ile Asp Tyr Gly Glu Met Lys Glu Ile Lys Gly Gly Arg Gly
            355                 360                 365

GAA TAT TCC AAG GCT CCT GAG CTC CTC TGG TCC CAG TGG TTC GAT TTT    1152
Glu Tyr Ser Lys Ala Pro Glu Leu Leu Trp Ser Gln Trp Phe Asp Phe
370                 375                 380

GGA CCG TTC AAA ATT GGA CCG AAT GGA CTC CTG CAC ACA GGG AAA ACC    1200
Gly Pro Phe Lys Ile Gly Pro Asn Gly Leu Leu His Thr Gly Lys Thr
385                 390                 395                 400

TTT AAA TTC CCT CTT TAT TTG ATC GGA GCA GGC ATA ATT GAC GAA GAT    1248
Phe Lys Phe Pro Leu Tyr Leu Ile Gly Ala Gly Ile Ile Asp Glu Asp
                405                 410                 415

CTG CAT GAA CTA GAT GAG GCT GCT CCC ATT GAT CAC CCA CAA ATG CCT    1296
Leu His Glu Leu Asp Glu Ala Ala Pro Ile Asp His Pro Gln Met Pro
            420                 425                 430

GAC GCG AAA AGC GTT CTT CCA GAA GAT GAA GAG ATA TTC TTC GGA GAC    1344
Asp Ala Lys Ser Val Leu Pro Glu Asp Glu Glu Ile Phe Phe Gly Asp
            435                 440                 445

ACA GGT GTA TCC AAA AAC CCT ATC GAG TTG ATT CAA GGA TGG TTC TCA    1392
Thr Gly Val Ser Lys Asn Pro Ile Glu Leu Ile Gln Gly Trp Phe Ser
450                 455                 460

AAT TGG AGA GAG AGT GTA ATG GCA ATA GTC GGA ATT GTT CTA CTC ATC    1440
Asn Trp Arg Glu Ser Val Met Ala Ile Val Gly Ile Val Leu Leu Ile
465                 470                 475                 480

GTT GTG ACA TTT CTG GCG ATC AAG ACG GTC CGG GTG CTT AAT TGT CTC    1488
Val Val Thr Phe Leu Ala Ile Lys Thr Val Arg Val Leu Asn Cys Leu
                485                 490                 495

TGG AGA CCC AGA AAG AAA AGA ATC GTC AGA CAA GAA GTA GAT GTT GAA    1536
Trp Arg Pro Arg Lys Lys Arg Ile Val Arg Gln Glu Val Asp Val Glu
            500                 505                 510

TCC CGA CTA AAC CAT TTT GAG ATG AGA GGC TTT CCT GAA TAT GTT AAG    1584
Ser Arg Leu Asn His Phe Glu Met Arg Gly Phe Pro Glu Tyr Val Lys
            515                 520                 525

AGA TAA                                                            1590
Arg
```

(2) INFORMATION FOR SEQ ID NO: 6:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asp Leu Phe Pro Ile Leu Val Val Leu Met Thr Asp Thr Val
1               5                   10                  15

Leu Gly Lys Phe Gln Ile Val Phe Pro Asp Gln Asn Glu Leu Glu Trp
                20                  25                  30

Arg Pro Val Val Gly Asp Ser Arg His Cys Pro Gln Ser Ser Glu Met
            35                  40                  45

Gln Phe Asp Gly Ser Arg Ser Gln Thr Ile Leu Thr Gly Lys Ala Pro
        50                  55                  60

Val Gly Ile Thr Pro Ser Lys Ser Asp Gly Phe Ile Cys His Ala Ala
65                  70                  75                  80
```

-continued

```
Lys Trp Val Thr Thr Cys Asp Phe Arg Trp Tyr Gly Pro Lys Tyr Ile
                 85                  90                  95

Thr His Ser Ile His His Leu Arg Pro Thr Thr Ser Asp Cys Glu Thr
            100                 105                 110

Ala Leu Gln Arg Tyr Lys Asp Gly Ser Leu Ile Asn Leu Gly Phe Pro
        115                 120                 125

Pro Glu Ser Cys Gly Tyr Ala Thr Val Thr Asp Ser Glu Ala Met Leu
    130                 135                 140

Val Gln Val Thr Pro His His Val Gly Val Asp Asp Tyr Arg Gly His
145                 150                 155                 160

Trp Ile Asp Pro Leu Phe Pro Gly Gly Glu Cys Ser Thr Asn Phe Cys
                165                 170                 175

Asp Thr Val His Asn Ser Ser Val Trp Ile Pro Lys Ser Gln Lys Thr
            180                 185                 190

Asp Ile Cys Ala Gln Ser Phe Lys Asn Ile Lys Met Thr Ala Ser Tyr
        195                 200                 205

Pro Ser Glu Gly Ala Leu Val Ser Asp Arg Phe Ala Phe His Ser Ala
    210                 215                 220

Tyr His Pro Asn Met Pro Gly Ser Thr Val Cys Ile Met Asp Phe Cys
225                 230                 235                 240

Glu Gln Lys Gly Leu Arg Phe Thr Asn Gly Glu Trp Met Gly Leu Asn
                245                 250                 255

Val Glu Gln Ser Ile Arg Glu Lys Lys Ile Ser Ala Ile Phe Pro Asn
            260                 265                 270

Cys Val Ala Gly Thr Glu Ile Arg Ala Thr Leu Glu Ser Glu Gly Ala
        275                 280                 285

Arg Thr Leu Thr Trp Glu Thr Gln Arg Met Leu Asp Tyr Ser Leu Cys
    290                 295                 300

Gln Asn Thr Trp Asp Lys Val Ser Arg Lys Glu Pro Leu Ser Pro Leu
305                 310                 315                 320

Asp Leu Ser Tyr Leu Ser Pro Arg Ala Pro Gly Lys Gly Met Ala Tyr
                325                 330                 335

Thr Val Ile Asn Gly Thr Leu His Ser Ala His Ala Lys Tyr Ile Arg
            340                 345                 350

Thr Trp Ile Asp Tyr Gly Glu Met Lys Glu Ile Lys Gly Gly Arg Gly
        355                 360                 365

Glu Tyr Ser Lys Ala Pro Glu Leu Leu Trp Ser Gln Trp Phe Asp Phe
    370                 375                 380

Gly Pro Phe Lys Ile Gly Pro Asn Gly Leu Leu His Thr Gly Lys Thr
385                 390                 395                 400

Phe Lys Phe Pro Leu Tyr Leu Ile Gly Ala Gly Ile Ile Asp Glu Asp
                405                 410                 415

Leu His Glu Leu Asp Glu Ala Ala Pro Ile Asp His Pro Gln Met Pro
            420                 425                 430

Asp Ala Lys Ser Val Leu Pro Glu Asp Glu Ile Phe Phe Gly Asp
        435                 440                 445

Thr Gly Val Ser Lys Asn Pro Ile Glu Leu Ile Gln Gly Trp Phe Ser
    450                 455                 460

Asn Trp Arg Glu Ser Val Met Ala Ile Val Gly Ile Val Leu Leu Ile
465                 470                 475                 480

Val Val Thr Phe Leu Ala Ile Lys Thr Val Arg Val Leu Asn Cys Leu
                485                 490                 495
```

```
Trp Arg Pro Arg Lys Lys Arg Ile Val Arg Gln Glu Val Asp Val Glu
            500                 505                 510

Ser Arg Leu Asn His Phe Glu Met Arg Gly Phe Pro Glu Tyr Val Lys
        515                 520                 525

Arg (2) INFORMATION FOR SEQ ID NO: 7:

(i) SEQUENCE CHARACTERISTICS:
        (A) LENGTH: 1590 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..1587

(xi) SEQUENCE DESCRIPTION: SEQ ID NO: 7:
```

| | | | | | | | | | | | | | | | | |
|---|---|---|---|---|---|---|---|---|---|---|---|---|---|---|---|---|
| ATG | GAT | CTC | TTT | CCC | ATT | TTG | GTC | GTG | GTG | CTC | ATG | ACA | GAT | ACT | GTC | 48 |
| Met | Asp | Leu | Phe | Pro | Ile | Leu | Val | Val | Val | Leu | Met | Thr | Asp | Thr | Val | |
| 1 | | | | 5 | | | | | 10 | | | | | 15 | | |
| TTA | GGG | AAG | TTT | CAA | ATT | GTC | TTC | CCG | GAT | CAG | AAT | GAA | CTG | GAG | TGG | 96 |
| Leu | Gly | Lys | Phe | Gln | Ile | Val | Phe | Pro | Asp | Gln | Asn | Glu | Leu | Glu | Trp | |
| | | | 20 | | | | | 25 | | | | | 30 | | | |
| AGA | CCA | GTT | GTG | GGT | GAC | TCT | CGG | CAT | TGC | CCA | CAG | TCA | TCA | GAA | ATG | 144 |
| Arg | Pro | Val | Val | Gly | Asp | Ser | Arg | His | Cys | Pro | Gln | Ser | Ser | Glu | Met | |
| | 35 | | | | | 40 | | | | | 45 | | | | | |
| CAA | TTC | GAT | GGA | AGC | AGA | TCC | CAG | ACC | ATA | CTG | ACT | GGG | AAA | GCT | CCC | 192 |
| Gln | Phe | Asp | Gly | Ser | Arg | Ser | Gln | Thr | Ile | Leu | Thr | Gly | Lys | Ala | Pro | |
| 50 | | | | | 55 | | | | | 60 | | | | | | |
| GTG | GGG | ATC | ACG | CCC | TCT | AAA | TCA | GAT | GGA | TTT | ATC | TGC | CAT | GCC | GCA | 240 |
| Val | Gly | Ile | Thr | Pro | Ser | Lys | Ser | Asp | Gly | Phe | Ile | Cys | His | Ala | Ala | |
| 65 | | | | | 70 | | | | | 75 | | | | | 80 | |
| AAA | TGG | GTG | ACA | ACA | TGT | GAT | TTC | AGG | TGG | TAT | GGG | CCG | AAA | TAC | ATC | 288 |
| Lys | Trp | Val | Thr | Thr | Cys | Asp | Phe | Arg | Trp | Tyr | Gly | Pro | Lys | Tyr | Ile | |
| | | | | 85 | | | | | 90 | | | | | 95 | | |
| ACT | CAT | TCA | ATA | CAT | CAT | CTG | AGA | CCG | ACA | ACA | TCA | GAC | TGT | GAG | ACA | 336 |
| Thr | His | Ser | Ile | His | His | Leu | Arg | Pro | Thr | Thr | Ser | Asp | Cys | Glu | Thr | |
| | | | 100 | | | | | 105 | | | | | 110 | | | |
| GCT | CTC | CAA | AGG | TAT | AAA | GAT | GGG | AGC | TTA | ATC | AAT | CTT | GGA | TTC | CCC | 384 |
| Ala | Leu | Gln | Arg | Tyr | Lys | Asp | Gly | Ser | Leu | Ile | Asn | Leu | Gly | Phe | Pro | |
| | | 115 | | | | | 120 | | | | | 125 | | | | |
| CCA | GAA | TCC | TGC | GGT | TAT | GCA | ACA | GTC | ACA | GAT | TCT | GAG | GCA | ATG | TTG | 432 |
| Pro | Glu | Ser | Cys | Gly | Tyr | Ala | Thr | Val | Thr | Asp | Ser | Glu | Ala | Met | Leu | |
| | 130 | | | | | 135 | | | | | 140 | | | | | |
| GTC | CAA | GTG | ACT | CCC | CAC | CAC | GTT | GGG | GTG | GAT | GAT | TAT | AGA | GGT | CAC | 480 |
| Val | Gln | Val | Thr | Pro | His | His | Val | Gly | Val | Asp | Asp | Tyr | Arg | Gly | His | |
| 145 | | | | | 150 | | | | | 155 | | | | | 160 | |
| TGG | ATC | GAC | CCA | CTA | TTT | CCA | GGA | GGA | GAA | TGC | TCC | ACC | AAT | TTT | TGT | 528 |
| Trp | Ile | Asp | Pro | Leu | Phe | Pro | Gly | Gly | Glu | Cys | Ser | Thr | Asn | Phe | Cys | |
| | | | | 165 | | | | | 170 | | | | | 175 | | |
| GAT | ACA | GTC | CAC | AAT | TCA | TCG | GTG | TGG | ATC | CCC | AAG | AGT | CAA | AAG | ACT | 576 |
| Asp | Thr | Val | His | Asn | Ser | Ser | Val | Trp | Ile | Pro | Lys | Ser | Gln | Lys | Thr | |
| | | | 180 | | | | | 185 | | | | | 190 | | | |
| GAC | ATC | TGT | GCC | CAG | TCT | TTC | AAA | AAT | ATC | AAG | ATG | ACC | GCA | TCT | TAC | 624 |
| Asp | Ile | Cys | Ala | Gln | Ser | Phe | Lys | Asn | Ile | Lys | Met | Thr | Ala | Ser | Tyr | |
| | | 195 | | | | | 200 | | | | | 205 | | | | |

```
CCC TCA GAA GGA GCA TTG GTG AGT GAC AGA TTT GCC TTC CAC AGT GCA      672
Pro Ser Glu Gly Ala Leu Val Ser Asp Arg Phe Ala Phe His Ser Ala
    210                 215                 220

TAT CAT CCA AAT ATG CCG GGG TCA ACT GTT TGC ATA ATG GAC TTT TGC      720
Tyr His Pro Asn Met Pro Gly Ser Thr Val Cys Ile Met Asp Phe Cys
225                 230                 235                 240

GAA CAA AAG GGG TTG AGA TTC ACA AAT GGA GAG TGG ATG GGT CTC AAT      768
Glu Gln Lys Gly Leu Arg Phe Thr Asn Gly Glu Trp Met Gly Leu Asn
                245                 250                 255

GTG GAG CAA TCC ATC CGA GAG AAG AAG ATA GTT GCC ATC TTC CCA AAT      816
Val Glu Gln Ser Ile Arg Glu Lys Lys Ile Ser Ala Ile Phe Pro Asn
            260                 265                 270

TGT GTT GCA GGG ACT GAA ATC CGA GCC ACA CTA GAA TCA GAA GGG GCA      864
Cys Val Ala Gly Thr Glu Ile Arg Ala Thr Leu Glu Ser Glu Gly Ala
        275                 280                 285

AGA ACT TTG ACG TGG GAG ACT CAA AGA ATG CTA GAT TAC TCT TTG TGT      912
Arg Thr Leu Thr Trp Glu Thr Gln Arg Met Leu Asp Tyr Ser Leu Cys
    290                 295                 300

CAG AAC ACC TGG GAC AAA GTT TCC AGG AAA GAA CCT CTC AGT CCG CTT      960
Gln Asn Thr Trp Asp Lys Val Ser Arg Lys Glu Pro Leu Ser Pro Leu
305                 310                 315                 320

GAC TTG AGC TAT CTG TCA CCA AGG GCT CCA GGG AAA GGC ATG GCC TAT     1008
Asp Leu Ser Tyr Leu Ser Pro Arg Ala Pro Gly Lys Gly Met Ala Tyr
                325                 330                 335

ACC GTC ATA AAC GGA ACC CTG CAT TCG GCT CAT GCT AAA TAC ATT AGA     1056
Thr Val Ile Asn Gly Thr Leu His Ser Ala His Ala Lys Tyr Ile Arg
            340                 345                 350

ACC TGG ATT GAT TAT GGA GAA ATG AAG GAA ATT AAA GGT GGA CGT GGA     1104
Thr Trp Ile Asp Tyr Gly Glu Met Lys Glu Ile Lys Gly Gly Arg Gly
        355                 360                 365

GAA TAT TCC AAG GCT CCT GAG CTC CTC TGG TCC CAG TGG TTC GAT TTT     1152
Glu Tyr Ser Lys Ala Pro Glu Leu Leu Trp Ser Gln Trp Phe Asp Phe
    370                 375                 380

GGA CCG TTC AAA ATT GGA CCG AAT GGA CTC CTG CAC ACA GGG AAA ACC     1200
Gly Pro Phe Lys Ile Gly Pro Asn Gly Leu Leu His Thr Gly Lys Thr
385                 390                 395                 400

TTT AAA TTC CCT CTT TAT TTG ATC GGA GCA GGC ATA ATT GAC GAA GAT     1248
Phe Lys Phe Pro Leu Tyr Leu Ile Gly Ala Gly Ile Ile Asp Glu Asp
                405                 410                 415

CTG CAT GAA CTA GAT GAG GCT GCT CCC ATT GAT CAC CCA CAA ATG CCT     1296
Leu His Glu Leu Asp Glu Ala Ala Pro Ile Asp His Pro Gln Met Pro
            420                 425                 430

GAC GCG AAA AGC GTT CTT CCA GAA GAT GAA GAG ATA TTC TTC GGA GAC     1344
Asp Ala Lys Ser Val Leu Pro Glu Asp Glu Glu Ile Phe Phe Gly Asp
        435                 440                 445

ACA GGT GTA TCC AAA AAC CCT ATC GAG TTG ATT CAA GGA TGG TTC TCA     1392
Thr Gly Val Ser Lys Asn Pro Ile Glu Leu Ile Gln Gly Trp Phe Ser
    450                 455                 460

AAT TGG AGA GAG AGT GTA ATG GCA ATA GTC GGA ATT GTT CTA CTC ATC     1440
Asn Trp Arg Glu Ser Val Met Ala Ile Val Gly Ile Val Leu Leu Ile
465                 470                 475                 480

GTT GTG ACA TTT CTG GCG ATC AAG ACG TCC CGG GTG CTT AAT TGT CTC     1488
Val Val Thr Phe Leu Ala Ile Lys Thr Val Arg Val Leu Asn Cys Leu
                485                 490                 495

TGG AGA CCC AGA AAG AAA AGA ATC GTC AGA CAA GAA GTA GAT GTT GAA     1536
Trp Arg Pro Arg Lys Lys Arg Ile Val Arg Gln Glu Val Asp Val Glu
            500                 505                 510
```

```
TCC CGA CTA AAC CAT TTT GAG ATG AGA GGC TTT CCT GAA TAT GTT AAG      1584
Ser Arg Leu Asn His Phe Glu Met Arg Gly Phe Pro Glu Tyr Val Lys
        515                 520                 525

AGA TAA                                                               1590
Arg
```

(2) INFORMATION FOR SEQ ID NO: 8:

(i) SEQUENCE CHARACTERISTICS:
        (A) LENGTH: 529 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Asp Leu Phe Pro Ile Leu Val Val Leu Met Thr Asp Thr Val
 1               5                  10                  15

Leu Gly Lys Phe Gln Ile Val Phe Pro Asp Gln Asn Glu Leu Glu Trp
                20                  25                  30

Arg Pro Val Val Gly Asp Ser Arg His Cys Pro Gln Ser Ser Glu Met
                35                  40                  45

Gln Phe Asp Gly Ser Arg Ser Gln Thr Ile Leu Thr Gly Lys Ala Pro
        50                  55                  60

Val Gly Ile Thr Pro Ser Lys Ser Asp Gly Phe Ile Cys His Ala Ala
 65                  70                  75                  80

Lys Trp Val Thr Thr Cys Asp Phe Arg Trp Tyr Gly Pro Lys Tyr Ile
                85                  90                  95

Thr His Ser Ile His His Leu Arg Pro Thr Thr Ser Asp Cys Glu Thr
                100                 105                 110

Ala Leu Gln Arg Tyr Lys Asp Gly Ser Leu Ile Asn Leu Gly Phe Pro
        115                 120                 125

Pro Glu Ser Cys Gly Tyr Ala Thr Val Thr Asp Ser Glu Ala Met Leu
        130                 135                 140

Val Gln Val Thr Pro His His Val Gly Val Asp Asp Tyr Arg Gly His
145                 150                 155                 160

Trp Ile Asp Pro Leu Phe Pro Gly Gly Glu Cys Ser Thr Asn Phe Cys
                165                 170                 175

Asp Thr Val His Asn Ser Ser Val Trp Ile Pro Lys Ser Gln Lys Thr
                180                 185                 190

Asp Ile Cys Ala Gln Ser Phe Lys Asn Ile Lys Met Thr Ala Ser Tyr
        195                 200                 205

Pro Ser Glu Gly Ala Leu Val Ser Asp Arg Phe Ala Phe His Ser Ala
        210                 215                 220

Tyr His Pro Asn Met Pro Gly Ser Thr Val Cys Ile Met Asp Phe Cys
225                 230                 235                 240

Glu Gln Lys Gly Leu Arg Phe Thr Asn Gly Glu Trp Met Gly Leu Asn
                245                 250                 255

Val Glu Gln Ser Ile Arg Glu Lys Lys Ile Ser Ala Ile Phe Pro Asn
                260                 265                 270

Cys Val Ala Gly Thr Glu Ile Arg Ala Thr Leu Glu Ser Glu Gly Ala
        275                 280                 285

Arg Thr Leu Thr Trp Glu Thr Gln Arg Met Leu Asp Tyr Ser Leu Cys
        290                 295                 300

Gln Asn Thr Trp Asp Lys Val Ser Arg Lys Glu Pro Leu Ser Pro Leu
305                 310                 315                 320
```

```
Asp Leu Ser Tyr Leu Ser Pro Arg Ala Pro Gly Lys Gly Met Ala Tyr
            325                 330                 335

Thr Val Ile Asn Gly Thr Leu His Ser Ala His Ala Lys Tyr Ile Arg
            340                 345                 350

Thr Trp Ile Asp Tyr Gly Glu Met Lys Glu Ile Lys Gly Gly Arg Gly
            355                 360                 365

Glu Tyr Ser Lys Ala Pro Glu Leu Leu Trp Ser Gln Trp Phe Asp Phe
    370                 375                 380

Gly Pro Phe Lys Ile Gly Pro Asn Gly Leu Leu His Thr Gly Lys Thr
385                 390                 395                 400

Phe Lys Phe Pro Leu Tyr Leu Ile Gly Ala Gly Ile Ile Asp Glu Asp
                405                 410                 415

Leu His Glu Leu Asp Glu Ala Ala Pro Ile Asp His Pro Gln Met Pro
                420                 425                 430

Asp Ala Lys Ser Val Leu Pro Glu Asp Glu Ile Phe Phe Gly Asp
            435                 440                 445

Thr Gly Val Ser Lys Asn Pro Ile Glu Leu Ile Gln Gly Trp Phe Ser
    450                 455                 460

Asn Trp Arg Glu Ser Val Met Ala Ile Val Gly Ile Val Leu Leu Ile
465                 470                 475                 480

Val Val Thr Phe Leu Ala Ile Lys Thr Val Arg Val Leu Asn Cys Leu
                485                 490                 495

Trp Arg Pro Arg Lys Lys Arg Ile Val Arg Gln Glu Val Asp Val Glu
                500                 505                 510

Ser Arg Leu Asn His Phe Glu Met Arg Gly Phe Pro Glu Tyr Val Lys
            515                 520                 525

Arg (2) INFORMATION FOR SEQ ID NO: 9:

(i) SEQUENCE CHARACTERISTICS:
        (A) LENGTH: 1569 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "DNA"

(ix) FEATURE:
        (A) NAME/KEY: CDS
        (B) LOCATION: 1..1566

(xi) SEQUENCE DESCRIPTION: SEQ ID NO: 9:

ATG AAT ATA CCT TGC TTT GCT GTG ATC CTC AGC TTA GCT ACT ACA CAT      48
Met Asn Ile Pro Cys Phe Ala Val Ile Leu Ser Leu Ala Thr Thr His
1               5                   10                  15

TCT CTG GGA GAA TTC CCC TTG TAT ACG ATT CCC GAG AAA ATA GAG AAA      96
Ser Leu Gly Glu Phe Pro Leu Tyr Thr Ile Pro Glu Lys Ile Glu Lys
                20                  25                  30

TGG ACC CCC ATA GAC ATG ATC CAT CTT AGT TGC CCT AAT AAC ATG CTG     144
Trp Thr Pro Ile Asp Met Ile His Leu Ser Cys Pro Asn Asn Met Leu
            35                  40                  45

TCT GAG GAA GAA GGT TGC AAT ACA GAG TCT CCT TTC ACC TAC TTC GAG     192
Ser Glu Glu Glu Gly Cys Asn Thr Glu Ser Pro Phe Thr Tyr Phe Glu
        50                  55                  60

CTC AAG AGT GGT TAC CTA GCC CAT CAG AAG GTC CCA GGA TTT ACA TGC     240
Leu Lys Ser Gly Tyr Leu Ala His Gln Lys Val Pro Gly Phe Thr Cys
65                  70                  75                  80
```

-continued

| | | |
|---|---|---|
| ACT GGG GTT GTG AAT GAG GCA GAG ACA TAC ACA AAC TTT GTC GGA TAT<br>Thr Gly Val Val Asn Glu Ala Glu Thr Tyr Thr Asn Phe Val Gly Tyr<br>                  85                  90                  95 | 288 |

```
ACT GGG GTT GTG AAT GAG GCA GAG ACA TAC ACA AAC TTT GTC GGA TAT        288
Thr Gly Val Val Asn Glu Ala Glu Thr Tyr Thr Asn Phe Val Gly Tyr
                85                  90                  95

GTC ACC ACC ACC TTC AAA AGG AAG CAC TTT AAA CCT ACA GTG GCT GCT        336
Val Thr Thr Thr Phe Lys Arg Lys His Phe Lys Pro Thr Val Ala Ala
            100                 105                 110

TGT CGT GAT GCC TAC AAC TGG AAA GTA TCA GGG GAC CCC CGA TAT GAA        384
Cys Arg Asp Ala Tyr Asn Trp Lys Val Ser Gly Asp Pro Arg Tyr Glu
                115                 120                 125

GAA TCT CTA CAC ACC CCG TAT CCC GAC AGC AGC TGG TTA AGG ACT GTG        432
Glu Ser Leu His Thr Pro Tyr Pro Asp Ser Ser Trp Leu Arg Thr Val
130                 135                 140

ACC ACA ACC AAA GAA GCC CTT CTT ATA ATA TCG CCA AGC ATT GTA GAG        480
Thr Thr Thr Lys Glu Ala Leu Leu Ile Ile Ser Pro Ser Ile Val Glu
145                 150                 155                 160

ATG GAC ATA TAT GGC AGG ACC CTT CAC TCT CCC ATG TTC CCT TCG GGG        528
Met Asp Ile Tyr Gly Arg Thr Leu His Ser Pro Met Phe Pro Ser Gly
                165                 170                 175

AAA TGT TCC AAG CTC TAT CCT TCT GTC CCC TCT TGT ACA ACC AAC CAT        576
Lys Cys Ser Lys Leu Tyr Pro Ser Val Pro Ser Cys Thr Thr Asn His
                180                 185                 190

GAT TAC ACA TTG TGG TTG CCA GAA GAT TCT AGT CTG AGT TTG ATT TGC        624
Asp Tyr Thr Leu Trp Leu Pro Glu Asp Ser Ser Leu Ser Leu Ile Cys
                195                 200                 205

GAC ATC TTC ACT TCC AGC AGT GGA CAG AAG GCC ATG AAT GGG TCT CGC        672
Asp Ile Phe Thr Ser Ser Ser Gly Gln Lys Ala Met Asn Gly Ser Arg
                210                 215                 220

ATC TGC GGA TTC AAG GAT GAA AGG GGA TTT TAC AGA TCC TTG AAG GGA        720
Ile Cys Gly Phe Lys Asp Glu Arg Gly Phe Tyr Arg Ser Leu Lys Gly
225                 230                 235                 240

TCC TGT AAG CTG ACA TTG TGC GGG AAA CCT GGA ATT AGG CTG TTC GAC        768
Ser Cys Lys Leu Thr Leu Cys Gly Lys Pro Gly Ile Arg Leu Phe Asp
                245                 250                 255

GGA ACT TGG GTC TCT TTT ACA AAG CCG GAC GTT CAT GTG TGG TGC ACT        816
Gly Thr Trp Val Ser Phe Thr Lys Pro Asp Val His Val Trp Cys Thr
                260                 265                 270

CCC AAC CAG TTA GTC AAT ATA CAT AAC GAC AGA CTA GAT GAG GTT GAA        864
Pro Asn Gln Leu Val Asn Ile His Asn Asp Arg Leu Asp Glu Val Glu
                275                 280                 285

CAT CTG ATC GTG GAC GAT ATC ATC AAG AAG AGA GAG TGT TTA GAC            912
His Leu Ile Val Asp Asp Ile Ile Lys Lys Arg Glu Glu Cys Leu Asp
290                 295                 300

ACG CTG GAA ACT ATA CTT ATG TCT CAA TCA GTT AGT TTT AGA CGG TTG        960
Thr Leu Glu Thr Ile Leu Met Ser Gln Ser Val Ser Phe Arg Arg Leu
305                 310                 315                 320

AGC CAT TTC AGA AAG TTA GTT CCA GGA TAT GGA AAA GCT TAC ACT ATT       1008
Ser His Phe Arg Lys Leu Val Pro Gly Tyr Gly Lys Ala Tyr Thr Ile
                325                 330                 335

TTG AAC GGC AGC TTA ATG GAA ACA AAT GTC TAC TAC AAA AGA GTT GAC       1056
Leu Asn Gly Ser Leu Met Glu Thr Asn Val Tyr Tyr Lys Arg Val Asp
                340                 345                 350

AGG TGG GCG GAC ATT TTG CCT TCT AGG GGA TGT CTG AAA GTC GGA CAA       1104
Arg Trp Ala Asp Ile Leu Pro Ser Arg Gly Cys Leu Lys Val Gly Gln
                355                 360                 365

CAG TGC ATG GAC CCT GTC AAA GGG GTC CTC TTC AAC GGA ATT ATC AAG       1152
Gln Cys Met Asp Pro Val Lys Gly Val Leu Phe Asn Gly Ile Ile Lys
                370                 375                 380

GGT CCG GAT GGA CAA ATA TTG ATT CCA GAG ATG CAG TCA GAG CAG CTC       1200
Gly Pro Asp Gly Gln Ile Leu Ile Pro Glu Met Gln Ser Glu Gln Leu
385                 390                 395                 400
```

```
AAA CAG CAT ATG GAT CTG TTG AAA GCA GCT ATG TTT CCT CTC CGT CAT      1248
Lys Gln His Met Asp Leu Leu Lys Ala Ala Met Phe Pro Leu Arg His
                405                 410                 415

CCT TTA ATC AAC AGA GAG GCA GTC TTC AAG AAG GAT GGA AAT GCC GAT      1296
Pro Leu Ile Asn Arg Glu Ala Val Phe Lys Lys Asp Gly Asn Ala Asp
            420                 425                 430

GAT TTT GTT GAT CTC CAT ATG CCT GAT GTT CAA AAA TCT GTG TCG GAT      1344
Asp Phe Val Asp Leu His Met Pro Asp Val Gln Lys Ser Val Ser Asp
        435                 440                 445

GTC GAC CTG GGC CTG CCT CAT TGG GGG TTC TGG TTG TTA GTC GGG GCA      1392
Val Asp Leu Gly Leu Pro His Trp Gly Phe Trp Leu Leu Val Gly Ala
    450                 455                 460

ACA GTA GTA GCC TTT GTG GTC TTG GCG TGC TTG CTC CGT GTA TGT TGT      1440
Thr Val Val Ala Phe Val Val Leu Ala Cys Leu Leu Arg Val Cys Cys
465                 470                 475                 480

AGG AGA ATG AGA AGG AGA AGG TCA CTG CGT GCC ACT CAG GAT ATC CCC      1488
Arg Arg Met Arg Arg Arg Arg Ser Leu Arg Ala Thr Gln Asp Ile Pro
                485                 490                 495

CTC AGC GTT GCC CCT GCC CCT GTC CCT CGT GCC AAA GTG GTG TCA TCA      1536
Leu Ser Val Ala Pro Ala Pro Val Pro Arg Ala Lys Val Val Ser Ser
            500                 505                 510

TGG GAG TCT TCT AAA GGG CTC CCA GGT ACT TGA                          1569
Trp Glu Ser Ser Lys Gly Leu Pro Gly Thr
        515                 520

(2) INFORMATION FOR SEQ ID NO: 10:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO: 10:

Met Asn Ile Pro Cys Phe Ala Val Ile Leu Ser Leu Ala Thr Thr His
 1               5                  10                  15

Ser Leu Gly Glu Phe Pro Leu Tyr Thr Ile Pro Glu Lys Ile Glu Lys
                20                  25                  30

Trp Thr Pro Ile Asp Met Ile His Leu Ser Cys Pro Asn Asn Met Leu
            35                  40                  45

Ser Glu Glu Gly Cys Asn Thr Glu Ser Pro Phe Thr Tyr Phe Glu
        50                  55                  60

Leu Lys Ser Gly Tyr Leu Ala His Gln Lys Val Pro Gly Phe Thr Cys
 65                  70                  75                  80

Thr Gly Val Val Asn Glu Ala Glu Thr Tyr Thr Asn Phe Val Gly Tyr
                85                  90                  95

Val Thr Thr Thr Phe Lys Arg Lys His Phe Lys Pro Thr Val Ala Ala
            100                 105                 110

Cys Arg Asp Ala Tyr Asn Trp Lys Val Ser Gly Asp Pro Arg Tyr Glu
        115                 120                 125

Glu Ser Leu His Thr Pro Tyr Pro Asp Ser Ser Trp Leu Arg Thr Val
    130                 135                 140

Thr Thr Thr Lys Glu Ala Leu Leu Ile Ile Ser Pro Ser Ile Val Glu
145                 150                 155                 160

Met Asp Ile Tyr Gly Arg Thr Leu His Ser Pro Met Phe Pro Ser Gly
                165                 170                 175
```

-continued

```
Lys Cys Ser Lys Leu Tyr Pro Ser Val Pro Ser Cys Thr Thr Asn His
            180             185             190

Asp Tyr Thr Leu Trp Leu Pro Glu Asp Ser Ser Leu Ser Leu Ile Cys
        195             200             205

Asp Ile Phe Thr Ser Ser Gly Gln Lys Ala Met Asn Gly Ser Arg
    210             215             220

Ile Cys Gly Phe Lys Asp Glu Arg Gly Phe Tyr Arg Ser Leu Lys Gly
225             230             235             240

Ser Cys Lys Leu Thr Leu Cys Gly Lys Pro Gly Ile Arg Leu Phe Asp
            245             250             255

Gly Thr Trp Val Ser Phe Thr Lys Pro Asp Val His Val Trp Cys Thr
            260             265             270

Pro Asn Gln Leu Val Asn Ile His Asn Asp Arg Leu Asp Glu Val Glu
            275             280             285

His Leu Ile Val Asp Asp Ile Ile Lys Lys Arg Glu Glu Cys Leu Asp
        290             295             300

Thr Leu Glu Thr Ile Leu Met Ser Gln Ser Val Ser Phe Arg Arg Leu
305             310             315             320

Ser His Phe Arg Lys Leu Val Pro Gly Tyr Gly Lys Ala Tyr Thr Ile
            325             330             335

Leu Asn Gly Ser Leu Met Glu Thr Asn Val Tyr Tyr Lys Arg Val Asp
            340             345             350

Arg Trp Ala Asp Ile Leu Pro Ser Arg Gly Cys Leu Lys Val Gly Gln
            355             360             365

Gln Cys Met Asp Pro Val Lys Gly Val Leu Phe Asn Gly Ile Ile Lys
    370             375             380

Gly Pro Asp Gly Gln Ile Leu Ile Pro Glu Met Gln Ser Glu Gln Leu
385             390             395             400

Lys Gln His Met Asp Leu Leu Lys Ala Ala Met Phe Pro Leu Arg His
            405             410             415

Pro Leu Ile Asn Arg Glu Ala Val Phe Lys Lys Asp Gly Asn Ala Asp
            420             425             430

Asp Phe Val Asp Leu His Met Pro Asp Val Gln Lys Ser Val Ser Asp
        435             440             445

Val Asp Leu Gly Leu Pro His Trp Gly Phe Trp Leu Leu Val Gly Ala
    450             455             460

Thr Val Val Ala Phe Val Val Leu Ala Cys Leu Leu Arg Val Cys Cys
465             470             475             480

Arg Arg Met Arg Arg Arg Ser Leu Arg Ala Thr Gln Asp Ile Pro
            485             490             495

Leu Ser Val Ala Pro Ala Pro Val Pro Arg Ala Lys Val Val Ser Ser
            500             505             510

Trp Glu Ser Ser Lys Gly Leu Pro Gly Thr
            515             520
```

TRANSGENIC ANIMALS

CROSS-REFERENCE TO RELATED APPLICATIONS

This is a continuation of application Ser. No. 09/329,749, filed Jun. 10, 1999, which issued on Sep. 18, 2001 as U.S. Pat. No. 6,291,740, which was a continuation-in-part of application Ser. No. 08/821,984, filed Mar. 19, 1997, which issued on Jun. 27, 2000 as U.S. Pat. No. 6,080,912.

STATEMENT REGARDING FEDERALLY SPONSORED RESEARCH OR DEVELOPMENT

Not applicable.

FIELD OF THE INVENTION

The present invention relates to improved methods for the generation of transgenic non-human animals. In particular, the present invention relates to the introduction of retroviral particles into the perivitelline space of gametes, zygotes and early stage embryos to allow the insertion of genetic material into the genome of the recipient gamete or embryo.

BACKGROUND OF THE INVENTION

The ability to alter the genetic make-up of animals, such as domesticated mammals such as cows, pigs and sheep, allows a number of commercial applications. These applications include the production of animals which express large quantities of exogenous proteins in an easily harvested form (e.g., expression into the milk), the production of animals which are resistant to infection by specific microorganisms and the production of animals having enhanced growth rates or reproductive performance. Animals which contain exogenous DNA sequences in their genome are referred to as transgenic animals.

The most widely used method for the production of transgenic animals is the microinjection of DNA into the pronuclei of fertilized embryos. This method is efficient for the production of transgenic mice but is much less efficient for the production of transgenic animals using large mammals such as cows and sheep. For example, it has been reported that 1,000 to 2,000 bovine embryos at the pronuclear stage must be microinjected to produce a single transgenic cow at an estimated cost of more than $500,000 (Wall et al., J. Cell. Biochem. 49:113 [1992]). Furthermore, microinjection of pronuclei is more difficult when embryos from domestic livestock (e.g., cattle, sheep, pigs) is employed as the pronuclei are often obscured by yolk material. While techniques for the visualization of the pronuclei are known (i.e., centrifugation of the embryo to sediment the yolk), the injection of pronuclei is an invasive technique which requires a high degree of operator skill.

Alternative methods for the production include the infection of embryos with retroviruses or with retroviral vectors. Infection of both pre- and post-implantation mouse embryos with either wild-type or recombinant retroviruses has been reported (Janenich, Proc. Natl. Acad. Sci. USA 73:1260 [1976]; Janenich et al., Cell 24:519 [1981]; Stuhlmann et al., Proc. Natl. Acad. Sci. USA 81:7151 [1984]; Jahner et al., Proc. Natl. Acad. Sci. USA 82:6927 [1985]; Van der Putten et al., Proc. Natl. Acad. Sci. USA 82:6148–6152 [1985]; Stewart et al., EMBO J. 6:383–388 [1987]). The resulting transgenic animals are typically mosaic for the transgene since incorporation occurs only in a subset of cells which form the transgenic animal. The consequences of mosaic incorporation of retroviral sequences (i.e., the transgene) include lack of transmission of the transgene to progeny due to failure of the retrovirus to integrate into the germ line, difficulty in detecting the presence of viral sequences in the founder mice in those cases where the infected cell contributes to only a small part of the fetus and difficulty in assessing the effect of the genes carried on the retrovirus.

In addition to the production of mosaic founder animals, infection of embryos with retrovirus (which is typically performed using embryos at the 8 cell stage or later) often results in the production of founder animals containing multiple copies of the retroviral provirus at different positions in the genome which generally will segregate in the offspring. Infection of early mouse embryos by co-culturing early embryos with cells producing retroviruses requires enzymatic treatment to remove the zona pellucida (Hogan et al., In Manipulating the Mouse Embryo: A Laboratory Manual, 2nd Ed., Cold Spring Harbor Laboratory Press, Cold Spring Harbor, N.Y., [1994], pp. 251–252). In contrast to mouse embryos, bovine embryos dissociate when removed from the zona pellucida. Therefore, infection protocols which remove the zona pellucida cannot be employed for the production of transgenic cattle or other animals whose embryos dissociate or suffer a significant decrease in viability upon removal of the zona pellucida (e.g., ovine embryos).

An alternative means for infecting embryos with retroviruses is the injection of virus or virus-producing cells into the blastocoele of mouse embryos (Jahner, D. et al., Nature 298:623 [1982]). As is the case for infection of eight cell stage embryos, most of the founders produced by injection into the blastocoele will be mosaic. The introduction of transgenes into the germline of mice has been reported using intrauterine retroviral infection of the midgestation mouse embryo (Jahner et al., supra [1982]). This technique suffers from a low efficiency of generation of transgenic animals and in addition produces animals which are mosaic for the transgene.

Infection of bovine and ovine embryos with retroviruses or retroviral vectors to create transgenic animals has been reported. These protocols involve the micro-injection of retroviral particles or growth arrested (i.e., mitomycin C-treated) cells which shed retroviral particles into the perivitelline space of fertilized eggs or early embryos (PCT International Application WO 90/08832 [1990]; and Haskell and Bowen, Mol. Reprod. Dev., 40:386 [1995]). PCT International Application WO 90/08832 describes the injection of wild-type feline leukemia virus B into the perivitelline space of sheep embryos at the 2 to 8 cell stage. Fetuses derived from injected embryos were shown to contain multiple sites of integration. The efficiency of producing transgenic sheep was low (efficiency is defined as the number of transgenics produced compared to the number of embryos manipulated); only 4.2% of the injected embryos were found to be transgenic. Haskell and Bowen (supra) describe the micro-injection of mitomycin C-treated cells producing retrovirus into the perivitelline space of 1 to 4 cell bovine embryos. The use of virus-producing cells precludes the delivery of a controlled amount of viral particles per embryo. The resulting fetuses contained between 2 and 12 proviruses and were shown to be mosaic for proviral integration sites, the presence of provirus, or both. The efficiency of producing transgenic bovine embryos was low; only 7% of the injected embryos were found to be transgenic.

The art needs improved methods for the production of transgenic animals, particularly for the production of transgenics using large domestic livestock animals. The ideal method would be simple to perform and less invasive than pronuclear injection, efficient, would produce mosaic transgenic founder animals at a low frequency and would result in the integration of a defined number of copies of the introduced sequences into the genome of the transgenic animal.

SUMMARY OF THE INVENTION

The present invention provides improved methods and compositions for the production of transgenic non-human animals. In one embodiment, the present invention provides a composition comprising a non-human unfertilized oocyte comprising a heterologous oligonucleotide (i.e., a heterologous polynucleotide) integrated into the genome of the oocyte. In a preferred embodiment the unfertilized oocyte is a pre-maturation oocyte. In another preferred embodiment the unfertilized oocyte is a pre-fertilization oocyte. The present invention is not limited by the nature of the heterologous oligonucleotide contained within the genome of the oocyte. In a preferred embodiment, the heterologous oligonucleotide is the proviral form of a retroviral vector.

The invention is not limited by the nature of the retroviral vector employed. Retroviral vectors containing a variety of genes may be employed. For example, the retroviral vector may contain sequences encoding proteins which modify growth rate, size and/or carcass composition (e.g., bovine growth hormone or other growth hormones) or foreign proteins of commercial value that are expressed in, and harvested from, a particular tissue component (e.g., blood or milk). The retroviral vector may contain genes that confer disease resistance to viruses or other microorganisms, including DNA sequences that are transcribed into RNA sequences that catalytically cleave specific RNAs (i.e., ribozymes) such as viral RNAs and DNA sequences that are transcribed into anti-sense RNA of an essential gene of a pathogenic microorganism. The above protein-encoding genes and DNA sequences are examples of "genes of interest."

The compositions of the present invention are not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a cow.

The present invention further provides a method for introducing a heterologous polynucleotide into the genome of a non-human unfertilized oocyte, comprising: a) providing: i) a non-human unfertilized egg comprising an oocyte having a plasma membrane and a zona pellucida, the plasma membrane and the zona pellucida defining a perivitelline space; ii) an aqueous solution comprising a heterologous polynucleotide; and b) introducing the solution comprising the heterologous polynucleotide into the perivitelline space under conditions which permit the introduction of the heterologous polynucleotide into the genome of the oocyte. The method of the present invention is not limited by the nature of the heterologous polynucleotide employed. In a preferred embodiment, the heterologous polynucleotide encodes a protein of interest. In a particularly preferred embodiment, the heterologous polynucleotide is contained within genome of a recombinant retrovirus.

The method of the present invention may be practiced using unfertilized eggs comprising a pre-maturation oocyte. Alternatively, the method of the present invention may employ pre-fertilization oocytes as the unfertilized egg.

When a recombinant retrovirus is employed infectious retroviral particles comprising the heterologous polynucleotide are preferentially employed. The method of the present invention is not limited by the nature of the infectious retrovirus employed to deliver nucleic acid sequences to an oocyte. Any retrovirus which is capable of infecting the species of oocyte to be injected may be employed. In a preferred embodiment, the infectious retrovirus comprises a heterologous membrane-associated protein. In a preferred embodiment, the heterologous membrane-associated protein is a G glycoprotein selected from a virus within the family Rhabdoviridae. In another preferred embodiment, the heterologous membrane associated protein is selected from the group consisting of the G glycoprotein of vesicular stomatitis virus, Piry virus, Chandipura virus, Spring viremia of carp virus and Mokola virus. In a particularly preferred embodiment, the heterologous membrane-associated protein is the G glycoprotein of vesicular stomatitis virus.

The method of the present invention is not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a cow.

The present invention further provides a method for the production of a transgenic non-human animal comprising: a) providing: i) an unfertilized egg comprising an oocyte having a plasma membrane and a zona pellucida, the plasma membrane and the zona pellucida defining a perivitelline space; ii) an aqueous solution containing infectious retrovirus; b) introducing the solution containing infectious retrovirus into the perivitelline space under conditions which permit the infection of the oocyte; and c) contacting the infected oocyte with sperm under conditions which permit the fertilization of the infected oocyte to produce an embryo. In a preferred embodiment, the method of the present invention further comprises, following the fertilization of the infected oocyte, the step of transferring the embryo into a hormonally synchronized non-human recipient animal (i.e., a female animal hormonally synchronized to stimulate early pregnancy). In another preferred embodiment, the method comprises the step of allowing the transferred embryo to develop to term. In still another referred embodiment, at least one transgenic offspring is identified from the offspring allowed to develop to term.

The method of the present invention may be practiced using unfertilized eggs comprising a pre-maturation oocyte. Alternatively, the method of the present invention may employ pre-fertilization oocytes as the unfertilized egg.

When pre-maturation oocytes are employed in the method of the present invention, the method may further comprise, following the introduction of the solution containing infectious retrovirus into the pre-maturation oocyte, the further step of culturing the infected pre-maturation oocyte under conditions which permit the maturation of the pre-maturation oocyte. The art is well aware of culture conditions which permit the in vitro maturation of pre-maturation oocytes from a variety of mammalian species.

The method of the present invention is not limited by the nature of the infectious retrovirus employed to deliver nucleic acid sequences to an oocyte. Any retrovirus which is capable of infecting the species of oocyte to be injected may be employed. In a preferred embodiment, the infectious retrovirus comprises a heterologous membrane-associated protein. In a preferred embodiment, the heterologous membrane-associated protein is a G glycoprotein selected from a virus within the family Rhabdoviridae. In another preferred embodiment, the heterologous membrane-associated protein is selected from the group consisting of the G glycoprotein of vesicular stomatitis virus, Piry virus, Chandipura virus, Spring viremia of carp virus and Mokola virus. In a particularly preferred embodiment, the heterologous membrane-associated protein is the G glycoprotein of vesicular stomatitis virus.

The method of the present invention is not limited by the nature of the non-human animal employed to provide oocytes. In a preferred embodiment, the non-human animal is a mammal (e.g., cows, pigs, sheep, goats, rabbits, rats, mice, etc.). In a particularly preferred embodiment, the non-human animal is a bovine.

The present invention further provides compositions comprising a stably maintained recombinant mammalian zygote, wherein the zygote comprises a polynucleotide containing the proviral form of a retroviral vector integrated into the genome of the zygote. In particularly preferred embodiments, the mammalian zygote is a bovine zygote, while in other preferred embodiments, the zygote is any mammalian zygote. Indeed, it is not intended that the present invention be limited to any particular animal species. In still other embodiments, the proviral form of the retroviral vector encodes a protein of interest. In yet further preferred embodiments, the recombinant retroviral vector comprises Moloney murine leukemia virus LTR. However, it is not intended that the present invention be limited to any particular retroviral LTR. Indeed, it is contemplated that other retroviral LTRS, including, but not limited, to mouse mammary tumor virus LTR, will find use in the present invention.

The present invention also provides methods for introducing a polynucleotide contained within the genome of a recombinant retrovirus into the genome of a mammalian zygote, comprising: a) providing: 1) a mammalian zygote having a plasma membrane and a zona pellucida, wherein the plasma membrane and zona pellucida define a perivitelline space; ii) an aqueous solution comprising a polynucleotide contained within the genome of a recombinant retrovirus; and b) introducing the solution comprising the polynucleotide contained within the genome of a recombinant retrovirus into the perivitelline space, under conditions which permit the introduction of the polynucleotide contained within the genome of the recombinant retrovirus into the genome of the zygote, such that the polynucleotide is stably maintained. In particularly preferred embodiments of the method, the efficiency of the introduction of the polynucleotide into the genome of the zygote is at least twenty percent. In still other embodiments, the efficiency ranges from approximately twenty percent to one hundred percent. In yet other preferred embodiments, the polynucleotide contained within the genome of the recombinant retrovirus encodes a protein of interest. In further embodiments, the method further comprises the step of transferring the zygote into a mammalian female recipient that is hormonally synchronized to simulate early pregnancy, thereby giving a transferred embryo. In other particularly preferred embodiments, the method further comprises the step of allowing the transferred embryo to develop to term. In further embodiments, the method comprises the additional step of identifying at least one transgenic offspring. In other particularly preferred embodiments, the present invention provides transgenic animals produced according to the above methods. In particularly preferred embodiments, the mammalian zygote is a bovine zygote, while in other preferred embodiments, the zygote is any other mammalian zygote. Indeed, is not intended that the present invention be limited to any particular animal species.

In still other embodiments of the above methods and transgenic animals, the recombinant retrovirus comprises Moloney murine leukemia virus long terminal repeat. However, it is not intended that the present invention be limited to any particular retroviral LTR. Indeed, it is contemplated that other retroviral LTRs, including, but not limited to mouse mammary tumor virus LTR, will find use in the present invention. In particularly preferred embodiments, the protein of interest is expressed by the transgenic offspring. In some embodiments, the protein of interest is expressed in at least one body fluid of the transgenic offspring. In some particularly preferred embodiments, the expression of the protein of interest is preferentially mammary-specific expression.

In further embodiments of the above methods and transgenic animals, the recombinant retrovirus comprises a heterologous membrane-associated protein. In some embodiments, the heterologous membrane-associated protein is a G glycoprotein selected from a virus within the family Rhabdoviridae. In other embodiments, the G glycoprotein is selected from the group comprising the G glycoprotein of vesicular stomatitis virus, Piry virus, Chandipura virus, Spring viremia of carp virus, Rabies virus, and Mokola virus.

The present invention also provides methods for producing transgenic non-human animals, wherein the genome of the transgenic non-human animal comprises a polynucleotide encoding a recombinant retrovirus and at least one protein of interest, comprising the steps of: a) providing: i) a non-human mammalian zygote having a plasma membrane and a zona pellucida, wherein the plasma membrane and the zona pellucida define a perivitelline space; ii) an aqueous solution comprising a polynucleotide contained within the genome of a recombinant retrovirus; b) introducing the solution comprising the polynucleotide contained within the genome of a recombinant retrovirus into the perivitelline space under conditions which permit the introduction of the polynucleotide contained within the genome of a recombinant retrovirus into the genome of the zygote, such that the polynucleotide is stably maintained in a recombinant zygote; c) transferring the recombinant zygote into a non-human female mammalian recipient that is hormonally synchronized to simulate early pregnancy, thereby giving a transferred embryo; d) allowing the transferred embryo to develop to term to produce a transgenic animal. In some particularly~embodiments, at least one protein of interest is expressed by the transgenic animal. In other preferred embodiments, the recombinant retrovirus comprises Moloney murine leukemia virus long terminal repeat. However, it is not intended that the present invention be limited to any particular retroviral LTR. Indeed, it is contemplated that other retroviral LTRS, including, but not limited to mouse mammary tumor virus LTR, will find use in the present invention.

In still other embodiments of the above methods, the efficiency of the introduction of the polynucleotide is at least twenty percent. In still other embodiments, the efficiency ranges from approximately twenty percent to one hundred percent. In further particularly preferred embodiments, the expression of the polynucleotide is preferentially mammary-specific expression. In other embodiments, the methods comprise the further step of mating the transgenic animal to a non-transgenic animal under conditions such that transgenic offspring are produced. In particularly preferred embodiments, the transgenic offspring express the polynucleotide. In other particularly preferred embodiments, the expression of the polynucleotide is mammary-specific expression. In yet other particularly preferred embodiments, the mammalian zygote is a bovine zygote, while in other preferred embodiments, the zygote is any other mammalian zygote. Indeed, is not intended that the present invention be limited to any particular animal species.

The present invention also provides methods for expressing a protein of interest, wherein the protein of interest is encoded by a polynucleotide contained within the genome of a recombinant retrovirus, comprising the steps of: a) providing: i) a non-human mammalian zygote having a plasma membrane and a zona pellucida, wherein the plasma membrane and the zona pellucida define a perivitelline space; ii) an aqueous solution comprising a polynucleotide encoding a protein of interest contained within the genome of a recombinant retrovirus; and b) introducing the solution comprising the polynucleotide encoding a protein of interest contained within the genome of a recombinant retrovirus into the perivitelline space, under conditions which permit the introduction of the polynucleotide contained within the genome of a recombinant retrovirus into the genome of the zygote, such that the polynucleotide is stably maintained; and c) allowing the zygote to develop into viable non-human animal, under conditions such that the protein of interest is expressed by the non-human animal.

In some preferred embodiments of the above methods, the recombinant retrovirus comprises Moloney murine leukemia virus long terminal repeat. However, it is not intended that the present invention be limited to any particular retroviral LTR., Indeed, it is contemplated that other retroviral LTRs, including, but not limited, to mouse mammary tumor virus LTR, will find use in the present invention. In yet other preferred embodiments, introduction of the polynucleotide into the genome of the zygote is at least twenty percent. In still other embodiments, the efficiency ranges from approximately twenty percent to one hundred percent. In yet other embodiments, the polynucleotide contained within the genome of a recombinant retrovirus encodes a viral protein. In other embodiments, viral protein is hepatitis B surface antigen. In still other embodiments, the present invention provides protein produced according to the above methods. In yet other embodiments, the method further comprises the step of harvesting the expressed protein of interest. In further embodiments, the expressed protein is expressed in the body fluids of the non-human animal. In particularly preferred embodiments, body fluids are selected from the group consisting of blood, milk, semen, and urine. In particularly preferred embodiments, the mammalian zygote is a bovine zygote, while in other preferred embodiments, the zygote is any mammalian zygote. Indeed, it is not intended that the present invention be limited to any particular animal species.

The present invention also provides methods for expressing a protein of interest wherein the protein of interest is encoded by a polynucleotide contained within the genome of a recombinant retrovirus, and the polynucleotide is integrated into the genome of a mammalian unfertilized oocyte, comprising the steps of. a) providing: i) an unfertilized mammalian egg comprising an oocyte having a plasma membrane and a zona pellucida, wherein the plasma membrane and the zona pellucida define a perivitelline space; ii) an aqueous solution containing recombinant retrovirus, wherein the recombinant retrovirus comprises a polynucleotide encoding a protein of interest; b) introducing the solution containing recombinant retrovirus into the perivitelline space under conditions which permit the infection of the oocyte to provide an infected oocyte; c) contacting the infected oocyte with sperm under conditions which permit the fertilization of the infected oocyte to produce an embryo; d) transferring the embryo into a hormonally synchronized mammalian recipient animal; e) allowing the embryo to develop into at least one viable transgenic mammalian animal, under conditions such that the protein of interest is expressed by the transgenic mammalian animal.

In some preferred embodiments, the unfertilized oocyte is a pre-maturation oocyte. In other embodiments, following the introduction of the solution containing infectious retrovirus into the pre-maturation oocyte, the method comprises the further step of culturing the infected pre-maturation oocyte under conditions which permit the maturation of the pre-maturation oocyte. In other preferred embodiments, the unfertilized oocyte is a pre-fertilization oocyte.

In still other preferred embodiments, the method further comprises the step of identifying at least one transgenic offspring. In particularly preferred embodiments, the mammal is a bovine. However, it is not intended that the present invention be limited to any particular animal species.

In further preferred embodiments, the recombinant retrovirus comprises Moloney murine leukemia virus long terminal repeat. However, it is not intended that the present invention be limited to any particular retroviral LTR. Indeed, it is contemplated that other retroviral LTRs, including, but not limited, to mouse mammary tumor virus LTR, will find use in the present invention. In yet other preferred embodiments, the expression of the protein of interest is preferentially mammary specific expression. In some particularly preferred embodiments of the method, the introduction of the polynucleotide into the genome of the infected oocyte, is greater than twenty percent. In still other embodiments, the efficiency ranges from approximately twenty percent to one hundred percent. In some preferred embodiments, the polynucleotide contained within the genome of a recombinant retrovirus encodes a viral protein. In some particularly preferred embodiments the viral protein is hepatitis B surface antigen. In alternative particularly preferred embodiments, the expressed protein is expressed in the body fluids of the mammalian animal. In some particularly preferred embodiments, the body fluids are selected from the group consisting of blood, milk, semen, and urine. In still other embodiments, the methods further comprise the step of f) harvesting the expressed protein of interest. The present invention also provides a protein of interest expressed using the above methods.

In yet other embodiments of the methods, the recombinant retrovirus comprises a heterologous membrane-associated protein. In some embodiments, the heterologous membrane-associated protein is a G glycoprotein selected from a virus within the family Rhabdoviridae. In yet other embodiments, the G glycoprotein is selected from the group comprising the G glycoprotein of vesicular stomatitis virus, Piry virus, Chandipura virus, Spring viremia of carp virus and Mokola virus.

from the blood and skin of calves derived from pre-fertilization oocytes and zygotes injected with pseudotyped LSRNL retrovirus.

Figure 4:
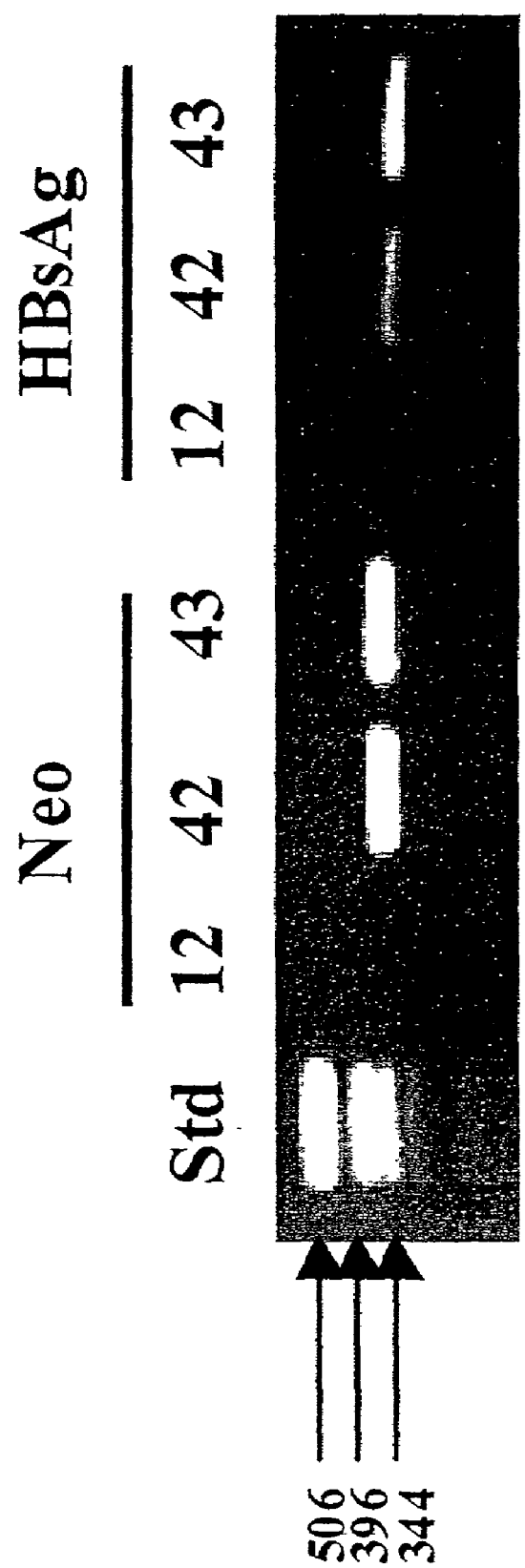

FIG. 4 shows an ethidium bromide stained agarose gel containing electrophoresed PCR products amplified using the neo gene primers (A) or HBsAg primers (B) from skin samples obtained from twin calves, who were offspring of a transgenic bull.

DEFINITIONS

To facilitate understanding of the invention, a number of terms are defined below.

As used herein, the term "egg," when used in reference to a mammalian egg, means an oocyte surrounded by a zona pellucida and a mass of cumulus cells (follicle cells) with their associated proteoglycan. The term "egg" is used in reference to eggs recovered from antral follicles in an ovary (these eggs comprise pre-maturation oocytes) as well as to eggs which have been released from an antral follicle (a ruptured follicle).

As used herein, the term "oocyte" refers to a female gamete cell and includes primary oocytes, secondary oocytes and mature, unfertilized ovum. An oocyte is a large cell having a large nucleus (i.e., the germinal vesicle) surrounded by ooplasm. The ooplasm contains non-nuclear cytoplasmic contents including mRNA, ribosomes, mitochondria, yolk proteins, etc. The membrane of the oocyte is referred to herein as the "plasma membrane."

The term "pre-maturation oocyte," as used herein refers to a female gamete cell following the oogonia stage (i.e., mitotic proliferation has occurred) that is isolated from an ovary (e.g., by aspiration) but which has not been exposed to maturation medium in vitro. Those of skill in the art know that the process of aspiration causes oocytes to begin the maturation process but that completion of the maturation process (i.e., formation of a secondary oocyte which has extruded the first polar body) in vitro requires the exposure of the aspirated oocytes to maturation medium. Pre-maturation oocytes will generally be arrested at the first anaphase of meiosis.

The term "pre-fertilization oocyte" as used herein, refers to a female gamete cell such as a pre-maturation oocyte following exposure to maturation medium in vitro but prior to exposure to sperm (i.e., matured but not fertilized). The pre-fertilization oocyte has completed the first meiotic division, has released the first polar body and lacks a nuclear membrane (the nuclear membrane will not reform until fertilization occurs; after fertilization, the second meiotic division occurs along with the extrusion of the second polar body and the formation of the male and female pronuclei). Pre-fertilization oocytes may also be referred to as matured oocytes at metaphase 11 of the second melosis.

The terms "unfertilized egg" or "unfertilized oocyte" as used herein, refers to any female gamete cell which has not been fertilized and these terms encompass both pre-maturation and pre-fertilization oocytes.

The term "zygote" as used herein, refers to a fertilized oocyte that has not yet undergone the first cleavage step in the development of an embryo (i.e., it is at the single-cell stage).

The term "perivitelline space" refers to the space located between the zona pellucida and the plasma membrane of a mammalian egg or oocyte.

As used herein, the term "trans" is used in reference to the positioning of genes of interest on the different strands of nucleic acid (e.g., alleles present on the two chromosomes of a chromosomal pair). The term "trans-acting" is used in reference to the controlling effect of a regulatory gene on a gene present on a different chromosome. In contrast to promoters, repressors are not limited in their binding to the DNA molecule that includes their genetic information. Therefore, repressors are sometimes referred to as transacting control elements.

The term "trans-activation" as used herein refers to the activation of gene sequences by factors encoded by a regulatory gene which is not necessarily contiguous with the gene sequences which it binds to and activates.

As used herein, the term "cis" is used in reference to the presence of genes on the same chromosome. The term "cis-acting" is used in reference to the controlling effect of a regulatory gene on a gene present on the same chromosome. For example, promoters, which affect the synthesis of downstream mRNA are cis-acting control elements.

As used herein, the term "retrovirus" is used in reference to RNA viruses which utilize reverse transcriptase during their replication cycle (i.e., retroviruses are incapable of replication; rather, these are useful RNA sequences that are packaged with at least two enzymes that are required for the insertion of the RNA sequences into the host cell genome). The retroviral genomic RNA is converted into double-stranded DNA by reverse transcriptase. This double-stranded DNA form of the virus integrates into the chromosome of the infected cell and is referred to as a "provirus." In preferred embodiments of the present invention, the term "proviral" is used in reference to constructs that are similar to "retrotransposons." These are integrated genes that are bracketed by LTRs in the host cell genome. However, in preferred embodiments, the proviral constructs cannot replicate. In contrast, in wild-type viruses, the provirus serves as a template for RNA polymerase 11 and directs the expression of RNA molecules which encode the structural proteins and enzymes needed to produce new viral particles. At each end of the provirus are structures called "long terminal repeats" or "LTRs". The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA As used herein, the term "provirus" is used in reference to a virus that is integrated into a host cell chromosome (or genome), and is transmitted from one cell generation to the next, without causing lysis or destruction of the host cell. The term is also used in reference to a duplex DNA sequence present in an eukaryotic chromosome, which corresponds to the genome of an RNA retrovirus.

As used herein, the term "endogenous virus" is used in reference to an inactive virus which is integrated into the chromosome of its host cell (often in multiple copies), and can thereby exhibit vertical transmission. Endogenous viruses can spontaneously express themselves and may result in malignancies.

As used herein, the terms "amphotrope" and "amphotropic" are used in reference to endogenous viruses that readily multiply in cells of the species in which they were induced, as well as cells of other species.

As used herein, the term "ecotrope" and "ecotropic" are used in reference to endogenous viruses that multiply readily in cells of the species in which they were induced, but cannot multiply in cells of other species.

As used herein, the term "xenotrope" and "xenotropic" are used in reference to endogenous viruses that cannot infect cells of the species in which they were induced, but can infect and multiply in cells of other species.

The term "Infectious retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell.

As used herein, the term "retroviral vector" is used in reference to retroviruses which have been modified so as to serve as vectors for introduction of nucleic acid into cells.

As used herein, the term "vector" is used in reference to nucleic acid molecules that transfer DNA segment(s) from one cell to another. Retroviral vectors transfer RNA, which is then reverse transcribed into DNA. The term "vehicle" is sometimes used interchangeably with "vector."

The term "expression vector" as used herein refers to a recombinant molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination," "in operable order," and "operably linked," as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "protein of interest" refers to any protein for which expression is desired. For example, the term encompasses any recombinant forms of a protein that is desired. The term "gene of interest" refers to any gene that is desired. In particularly preferred embodiments, the gene of interest encodes at least a portion of a protein of interest.

The term "genetic cassette" as used herein refers to a fragment or segment of nucleic acid containing a particular grouping of genetic elements. The cassette can be removed and inserted into a vector or plasmid as a single unit.

As used herein, the term "long terminal repeat (LTR)" is used in reference to domains of base pairs located at the ends of retroviral DNA's. These LTRs may be several hundred base pairs in length. LTR's often provide functions fundamental to the expression of most eukaryotic genes (e.g., promotion, initiation and polyadenylation of transcripts).

Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells which are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell.

The terms "vector particle" or "retroviral particle" refer to viral-like particles that are capable of introducing nucleic acid into a cell through a viral-like entry mechanism.

The host range of a retroviral vector (i.e., the range of cells that these vectors can infect) can be altered by including an envelope protein from another closely related virus.

As used herein, the term "packaging signal" or "packaging sequence" refers to non-coding sequences located within the retroviral genome which are required for insertion of the viral RNA into the viral capsid or particle. Several retroviral vectors use the minimal packaging signal (also referred to as the psi sequence) needed for encapsidation of the viral genome. This minimal packaging signal encompasses bases 212 to 563 of the Mo-MuLV genome (Mann et al., Cell 33:153 [1983]).

As used herein, the term "extended packaging signal" or "extended packaging sequence" refers to the use of sequences around the psi sequence with further extension into the gag gene. In Mo-MuLV, this extended packaging sequence corresponds to the region encompassing base 1039 to base 1906 (Akagi et al., Gene 106:255 [1991]). The frequently used M-MuLV vector, pLNL6 (Bender et al., J. Virol., 61:1639 [1987]), contains the entire 5~region of the genome including an extended packaging signal from bases 206 to 1039 of the Moloney murine sarcoma virus genome (numbering from Supplements and Appendices in RNA Tunior Viruses, 2nd Ed. [1985] pp. 986–988). The inclusion of these additional packaging sequences increases the efficiency of insertion of vector RNA into viral particles.

As used herein, the term "packaging cell lines" is used in reference to cell lines that express viral structural proteins (e.g., gag, pol and env), but do not contain a packaging signal.

When retroviral vector DNA is transfected into the cells, it becomes integrated into the chromosomal DNA and is transcribed, thereby producing full-length retroviral vector RNA that has a psi-sequence. Under these conditions, only the vector RNA is packaged into the viral capsid structures These complete, yet replication-defective, virus particles can then be used to deliver the retroviral vector to target cells with relatively high efficiency.

The term "transfection" as used herein refers to the introduction of foreign DNA into eukaryotic cells. Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. In contrast, as used herein, the term "transduction" refers to the delivery of a gene(s) using a retroviral vector by means of infection rather than by transfection.

The term "membrane-associated protein" refers to a protein (e.g., a viral envelope glycoprotein or the G proteins of viruses in the Rhabdoviridae family such as VSV, Piry, Chandipura and Mokola) which are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus which is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus which includes vesicular stomatitis-virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmitic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein. The term "conditions which permit the maturation of a pre-maturation oocyte" refers to conditions of in vitro cell culture which permit the maturation of a pre-maturation oocyte to a mature ovum (e.g., a pre-fertilization oocyte). These culture conditions permit and induce the events which are associated with maturation of the pre-maturation oocyte including stimulation of the first and second meiotic divisions. In vitro culture conditions which permit the maturation of pre-maturation oocytes from a variety of mammalian species (e.g., cattle, hamster, pigs and goats) are well know to the art (See e.g., Parrish et al., Therlogenol., 24:537 [19851; Rosenkrans and First, J. Anim. Sci., 72:434 [1994]; Bavister and Yanagimachi, Biol. Reprod., 16:228 [1977]; Bavister et al., Biol. Reprod., 28:235 [1983]; Leibfried and Bavister, J. Reprod. Fert., 66:87 [1982]; Keskintepe et al., Zygote 2:97 [1994]; Funahashi et al., I Reprod. Fert., 101:159 [19941; and Funahashi et al., Biol. Reprod 50:1072 [1994].

As used herein, the term "remedial gene" refers to a gene whose expression is desired in a cell to correct an error in cellular metabolism, to inactivate a pathogen or to kill a cancerous cell.

As used herein, the term "selectable marker" refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpi gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt) gene which is used in conjunction with hprt-cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp. 16.9–16.15.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: Tm=81.5+0.41 (% G+C), when a nucleic acid is in aqueous solution at 1 M NaCI (See e.g., Anderson and Young, Quantitative Filter Hybridization, in *Nucleic Acid Hybridization* (1985). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, which is capable of hybridizing to another oligonucleotide of interest. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is further contemplated that the oligonucleotide of interest (i.e., to be detected) will be labelled with a reporter molecule. It is also contemplated that both the probe and oligonucleotide of interest will be labelled. It is not intended that the present invention be limited to any particular detection system or label.

As used herein, the term "target" refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are the to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of "P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of QP replicase, MDV-I RNA is the specific template for the replicase (Kacian et al., Proc. Nat. Acad. Sci USA 69:3038 [1972]). Other nucleic acid will not be replicated by this amplification enzyme. Similarly, in the case of T7 RNA polymerase, this amplification enzyme has a stringent specificity for its own promoters (M. Chamberlin et. al., Nature 228:227 [1970]). In the case of T4 DNA ligase, the enzyme will not ligate the two oligonucleotides where there is a mismatch between the oligonucleotide substrate and the template at the ligation junction (Wu and Wallace, Genomics 4:560 [1989]). Finally, thermostable polymerases, such as Taq and Pfii, by virtue of their ability to function at high temperature, are found to display high specificity for the sequences bounded and thus defined by the primers; the high temperature results in thermodynamic conditions that favor primer hybridization with the target sequences and not hybridization with non-target sequences.

Some amplification techniques take the approach of amplifying and then detecting target; others detect target and then amplify probe. Regardless of the approach, nucleic acid must be free of inhibitors for amplification to occur at high efficiency.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR (Mullis, et al., Cold Spring Harbor Symposia, Vol. 11, pp. 263–273 [1986]). Because the nested primers anneal to the target inside the annealing boundaries of the starting primers, the predominant PCR-amplified product of the starting primers is necessarily a longer sequence, than that defined by the annealing boundaries of the nested primers. The PCR-amplified product of the nested primers is an amplified segment of the target sequence that cannot, therefore, anneal with the starting primers. Advantages to the use of nested primers include the large degree of specificity, as well as the fact that a smaller sample portion may be used and yet obtain specific and efficient amplification.

As used herein, the term "amplification reagents" refers to those reagents (deoxyribonucleoside triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotidesequence.

As used herein, the term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "Y end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a DNA sequence comprising the coding region of a gene or in other words the DNA sequence which encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "transcription unit" refers to the segment of DNA between the sites of initiation and termination of transcription and the regulatory elements necessary for the efficient initiation and termination. For example, a segment of DNA comprising an enhancer/promoter, a coding region and a termination and polyadenylation sequence comprises a transcription unit.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss et al., Trends Biochem. Sci., 11:287 [1986]; and Maniatis et al., supra [1987]). For example, the SV40 early gene enhancer is very active in a wide variety of cell types from many mammalian species and has been widely used for the expression of proteins in mammalian cells (Dijkema et al., EMBO J., 4:761 [1985]). Two other examples of promoter/enhancer elements active in a broad range of mammalian cell types are those from the human elongation factor la gene (Uetsuki ef al., J. Biol. Chem., 264:5791 [1989]; Kim et al., Gene 91:217 [1990]; and Mizushima and Nagata, Nue. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "flexogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The term "factor" refers to a protein or group of proteins necessary for the transcription or replication of a DNA sequence. For example, SV40 T antigen is a replication factor which is necessary for the replication of DNA sequences containing the SV40 origin of replication. Transcription factors are proteins which bind to regulatory elements such as promoters and enhancers and facilitate the initiation of transcription of a gene.

Promoters and enhancers may bind to specific factors which increase the rate of activity from the promoter or enhancer. These factors may be present in all cell types or may be expressed in a tissue-specific manner or in virus infected cells. In the absence of such a factor the promoter may be inactive or may produce a low level of transcriptional activity. Such a low level of activity is referred to as a baseline or "basal" rate of activity. Additionally, viral promoter and enhancers may bind to factors encoded by the virus such that the viral promoter or enhancer is "activated" in the presence of the viral factor (in a virus infected cell or in a cell expressing the viral factor). The level of activity in the presence of the factor (i.e., activity "induced" by the factor) will be higher than the basal rate.

Different promoters may have different levels of basal activity in the same or different cell types. When two different promoters are compared in a given cell type in the absence of any inducing factors, if one promoter expresses at a higher level than the other it is said to have a higher basal activity.

The activity of a promoter and/or enhancer is measured by detecting directly or indirectly the level of transcription from the element(s). Direct detection involves quantitating the level of the RNA transcripts produced from that promoter and/or enhancer. Indirect detection involves quantitation of the level of a protein, often an enzyme, produced from RNA transcribed from the promoter and/or enhancer. An commonly employed assay for promoter or enhancer activity utilizes the chloramphenicol acetyltransferase (CAT) gene. A promoter and/or enhancer is inserted upstream from the coding region for the CAT gene on a plasmid; the plasmid is introduced into a cell line. The levels of CAT enzyme are measured. The level of enzymatic activity is proportional to the amount of CAT RNA transcribed by the cell line. This CAT assay therefore allows a comparison to be made of the relative strength of different promoters or enhancers in a given cell line. When a promoter is said to express at "high" or "low" levels in a cell line this refers to the level of activity relative to another promoter which is used as a reference or standard of promoter activity.

The presence of "splicing signals" on an expression vector often results in higher levels of expression of the recombinant transcript. Splicing signals mediate the removal of introns from the primary RNA transcript and consist of a splice donor and acceptor site (See e.g., Sambrook, J. et al., Molecular Cloning: A Laboratory Manual, 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are 10 rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The Sv40 poly A signal is contained on a 237 bp Bam HUM I restriction fragment and directs both termination and polyadenylation (Sambrook, J., supra, at 16.6–16.7).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the SV40 or polyoma virus origin of replication replicate to high copy number (up to 104 copies/cell) in cells that express the appropriate viral antigen. Vectors which contain the replicons from bovine papillornavirus or Epstein-Barr virus replicate extrachromosomally at low copy number (~100 copies/cell).

The term "stable transfection" or "stably transfected" refers to the introduction and integration of foreign DNA into the genome of the transfected cell. The term "stable transfectant" refers to a cell which has stably integrated foreign DNA into the genomic DNA.

As used herein, the term "stably maintained" refers to characteristics of recombinant (i.e., transgenic) animals that maintain at least one of their recombinant elements (i.e., the element that is desired) through multiple generations. For example, it is intended that the term encompass the characteristics of transgenic animals that are capable of passing the transgene to their offspring, such that the offspring are capable of maintaining the expression and/or transcription of the transgene. It is not intended that the term be limited to any particular organism or any specific recombinant element.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "gene of interest" refers to the gene inserted into the polylinker of an expression vector. When the gene of interest encodes a gene which provides a therapeutic function, the gene of interest may be alternatively called a remedial gene.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "adoptive transfer" is used in reference to the transfer of one function to another cell or organism. For example, in "adoptive immunity," transfer of an immune function is made from one organism to another through the transfer of immunologically competent cells.

DESCRIPTION OF THE INVENTION

The present invention provides improved methods for the production of transgenic animals. The methods of the present invention provide, for the first time, the production of transgenic animals by the introduction of exogenous DNA into pre-maturation oocytes and mature, unfertilized oocytes (i.e., pre-fertilization oocytes) using retroviral vectors which transduce dividing cells (e.g., vectors derived from murine leukemia virus [MLV]). In addition, the present invention provides methods and compositions for cytomegalovirus promoter-driven, as well as mouse mammary tumor LTR expression of various recombinant proteins.

For example, the human Cytomegalovirus (CMV) promoter has been developed for use in retroviral vectors for driving the expression of various recombinant proteins, and cell lines have been infected with these vectors, with resultant recombinant protein expression. In addition, the mouse mammary tumor virus (MMTV) LTR has been previously shown to control expression of a recombinant protein in transgenic mice (Yom et al., Animal Biotech., 4:89–107 [1993]). In these mouse lines, expression was predominately observed in the mammary gland and milk, but low expression was also observed in the salivary gland, spleen, lung and kidney. The transgenic mice used in this experiment were produced using typical microinjection techniques. In contrast, the present invention provides methods and compositions for the use of MMTV LTR-driven expression which avoids the need for microinjection techniques. For example, the MMTV LTR has been developed for use in retroviral vectors for driving the expression of various recombinant proteins, and cell lines have been infected with these vectors, with resultant recombinant protein expression.

The following Description of the Invention is divided into the following sections: I. Retroviruses and Retroviral Vectors; II. Integration of Retroviral DNA; III. Introduction of Retroviral Vectors Into Gametes Before the Last Melotic Division; IV. Detection of the Retrovirus Following Injection Into Oocytes or Embryos; and V. Expression of Foreign Proteins in Transgenic Animals.

I. Retroviruses and Retroviral Vectors

Retroviruses (family Retroviridae) are divided into three groups: the spurnaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genorne as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products) which is surrounded by a lipid bilayer membrane derived from the host cell containing the viral envelope glycoproteins (also referred to as membrane-associated proteins).

The organization of the genomes of numerous retroviruses is well known in the art and this has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [–PBS], the 3' regulatory sequences required for reverse transcription [+PBS] and the viral LTRS). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes which are essential for viral replication (these essential genes are either deleted or disabled); the resulting virus is said to be replication defective.

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles which lack a membrane-associated protein (e.g., an env protein). In order to produce viral particles containing a membrane associated protein which will permit entry of the virus into a cell, the packaging cell line containing the retroviral sequences is transfected with sequences encoding a membrane-associated protein (e.g., the G protein of vesicular stornatitis virus [VSV]). The transfected packaging cell will then produce viral particles which contain the membrane-associated protein expressed by the transfected packaging cell line; these viral particles which contain viral genomic RNA derived from one virus encapsidated by the envelope proteins of another virus are said to be pseudotyped virus particles. of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (Miller and Baltimore, Mol. Cell. Biol., 6:2895 [19861]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Despite these advantages, existing retroviral vectors based upon MoMLV are limited by several intrinsic problems: 1) they do not infect non-dividing cells (Miller et al., Mol. Cell. Biol., 10:4239 [1992]), 2) they produce low titers of the recombinant virus (Miller and Rosman, BioTechn., 7: 980 [1989]; and Miller, Nature 357: 455 [1992]) and 3) they infect certain cell types (e.g., human lymphocytes) with low efficiency (Adams et al., Proc. Natl. Acad. Sci. USA 89:8981 [1992]). The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al., Proc. Natl. Acad. Sci. USA 90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

The present invention is not limited to the use of the VSV G protein when a viral G protein is employed as the heterologous membrane-associated protein within a viral particle. The G proteins of viruses in the Vesiculovirus genera other than VSV, such as the Piry and Chandipura viruses, that are highly homologous to the VSV G protein and, like the VSV G protein, contain covalently linked palmitic acid (Brun et al., Intervirol., 38:274 [1995]; and Masters et al., Virol., 171:285 [1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol., 69:1444 [1995]). The nucleotide sequence encoding the Piry G protein is provided in SEQ ID NO:5 and the amino acid sequence of the Piry G protein is provided in SEQ ID NO:6. The nucleotide sequence encoding the Chandipura G protein is provided in SEQ ID NO:7 and the amino acid sequence of the Chandipura G protein is provided in SEQ ID NOX The nucleotide sequence encoding the Mokola G protein is provided in SEQ ID NO:9 and the amino acid sequence of the Mokola G protein is provided in SEQ ID NO:10. Viral particles may be pseudotyped using either the Piry, Chandipura or Mokola G protein as described in Example 2 with the exception that a plasmid containing sequences encoding either the Piry, Chandipura or Mokola G protein under the transcriptional control of a suitable promoter element (e.g., the CMV intermediate early promoter; numerous expression vectors containing the CMV IE promoter are available, such as the pcDNA3.1 vectors [Invitrogen]) is used in place of pHCMV-G. Sequences encoding other G proteins derived from other members of the Rhabdoviridae family may be used; sequences encoding numerous rhabdoviral G proteins are available from the GenBank database.

II. Integration of Retroviral DNA

The majority of retroviruses can transfer or integrate a double-stranded linear form of the virus (the provirus) into the genome of the recipient cell only if the recipient cell is cycling (i.e., dividing) at the time of infection. Retroviruses which have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J., 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

III. Introduction of Retroviral Vectors into Gametes Before the Last Meiotic Division The nuclear envelope of a cell breaks down during melosis as well as during mitosis. Meiosis occurs only during the final stages of gametogenesis. The methods of the present invention exploit the breakdown of the nuclear envelope during meiosis to permit the integration of recombinant retroviral DNA and permit for the first time the use of unfertilized oocytes (i.e., pre-fertilization and pre-maturation oocytes) as the recipient cell for retroviral gene transfer for the production of transgenic animals. Because infection of unfertilized oocytes permits the integration of the recombinant provirus prior to the division of the one cell embryo, all cells in the embryo will contain the proviral sequences.

Oocytes which have not undergone the final stages of gametogenesis are infected with the retroviral vector. The injected oocytes are then permitted to complete maturation with the accompanying melotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions which permit maturation of the oocyte prior to fertilization in vitro. Conditions for the maturation of oocytes from a number of mammalian species (e.g., bovine, ovine, porcine, murine, caprine) are well known to the art. In general, the base medium used herein for the in vitro maturation of bovine oocytes, TC-M199 medium, may be used for the in vitro maturation of other mammalian oocytes. TC-M199 medium is supplemented with hormones (e.g., luteinizing hormone and estradiol) from the appropriate mammalian species. The amount of time a pre-maturation oocyte must be exposed to maturation medium to permit maturation varies between mammalian species as is known to the art. For example, an exposure of about 24 hours is sufficient to permit maturation of bovine oocytes while porcine oocytes require about 44–48 hours.

Oocytes may be matured in vivo and employed in place of oocytes matured in vitro in the practice of the present invention. For example, when porcine oocytes are to be employed in the methods of the present invention, matured pre-fertilization oocytes may be harvested directly from pigs that are induced to superovulate as is known to the art. Briefly, on day 15 or 16 of estrus the female pig(s) is injected with about 1000 units of pregnant mare's serum (PMS; available from Sigma and Calbiochem). Approximately 48 hours later, the pig(s) is injected with about 1000 units of human chorionic gonadotropin) (hCG; Sigma) and 24–48 hours later matured oocytes are collected from oviduct. These in vivo matured pre-fertilization oocytes are then injected with the desired retroviral preparation as described herein. Methods for the superovulation and collection of in vivo matured (i.e., oocytes at the metaphase 2 stage) oocytes are known for a variety of mammals (e.g., for superovulation of mice, see Hogan et al., supra at pp. 130–133 [1994]; for superovulation of pigs and in vitro fertilization of pig oocytes see Cheng, Doctoral Dissertation, Cambridge University, Cambridge, United Kingdom [1995]).

Retroviral vectors capable of infecting the desired species of non-human animal which can be grown and concentrated to very high titers (e.g., $\geq$: $1\times10^8$ cfu/ml) are preferentially employed. The use of high titer virus stocks allows the introduction of a defined number of viral particles into the perivitelline space of each injected oocyte. The perivitelline space of most mammalian oocytes can accommodate about 10 picoliters of injected fluid (those in the art know that the volume that can be injected into the perivitelline space of a mammalian oocyte or zygote varies somewhat between species as the volume of an oocyte is smaller than that of a zygote and thus, oocytes can accommodate somewhat less than can zygotes).

The vector used may contain one or more genes encoding a protein of interest; alternatively, the vector may contain sequences which produce anti-sense RNA sequences or ribozymes. The infectious virus is microinjected into the perivitelline space of oocytes (including pre-maturation oocytes) or one cell stage zygotes. Microinjection into the perivitelline space is much less invasive than the microinjection of nucleic acid into the pronucleus of an embryo. Pronuclear injection requires the mechanical puncture of the plasma membrane of the embryo and results in lower embryo viability. In addition, a higher level of operator skill is required to perform pronuclear injection as compared to perivitelline injection. Visualization of the pronucleus is not required when the virus is injected into the perivitelline space (in contrast to injection into the pronucleus); therefore injection into the perivitelline space obviates the difficulties associated with visualization of pronuclei in species such as cattle, sheep and pigs.

The virus stock may be titered and diluted prior to microinjection into the perivitelline space so that the number of proviruses integrated in the resulting transgenic animal is controlled. The use of a viral stock (or dilution thereof) having a titer of $1\times10^8$ cfu/ml allows the delivery of a single viral particle per oocyte. The use of pre-maturation oocytes or mature fertilized oocytes as the recipient of the virus minimizes the production of animals which are mosaic for the provirus as the virus integrates into the genome of the oocyte prior to the occurrence of cell cleavage.

In order to deliver, on average, a single infectious particle per oocyte, the micropipets used for the injection are calibrated as follows. Small volumes (e.g., about 5–10 pl) of the undiluted high titer viral stock (e.g., a titer of about $1\times10^8$ cfU/ml) are delivered to the wells of a microtiter plate by pulsing the micromanipulator. The titer of virus delivered per a given number of pulses is determined by diluting the viral stock in each well and determining the titer using a suitable cell line (e.g., the 208F cell line) as described in Ex. 2. The number of pulses which deliver, on average, a volume of virus stock containing one infectious viral particle (i.e., gives a MOI of 1 when titered on 208F cells) are used for injection of the viral stock into the oocytes.

Prior to microinjection of the titered and diluted (if required) virus stock, the cumulus cell layer is opened to provide access to the perivitelline space. The cumulus cell layer need not be completely removed from the oocyte and indeed for certain species of animals (e.g., cows, sheep, pigs, mice) a portion of the cumulus cell layer must remain in contact with tile oocyte to permit proper development and fertilization post-injection. Injection of viral particles into the perivitelline space allows the vector RNA (i.e., the viral genome) to enter the cell through the plasma membrane thereby allowing proper reverse transcription of the viral RNA.

IV. Detection of the Retrovirus Following Injection into Oocytes or Embryos

The presence of the retroviral genome in cells (e.g., oocytes or embryos) infected with pseudotyped retrovirus may be detected using a variety of means. The expression of the gene product(s) encoded by the retrovirus may be detected by detection of mRNA corresponding to the vector-encoded gene products using techniques well known to the art (e.g., Northern blot, dot blot, in situ hybridization and RT-PCR analysis). Direct detection of the vector-encoded gene product(s) is employed when the gene product is a protein which either has an enzymatic activity (e.g., P-galactosidase) or when an antibody capable of reacting with the vector encoded protein is available.

Alternatively, the presence of the integrated viral genome may be detected using Southern blot or PCR analysis. For example, the presence of the LZRNL or LSRNL genomes may be detected following infection of oocytes or embryos using PCR as follows. Genomic DNA is extracted from the infected oocytes or embryos (the DNA may be extracted from the whole embryo or alternatively various tissues of the embryo may be examined) using techniques well known to the art. The LZRNL and LSRNL viruses contain the neo gene and the following primer pair can be used to amplify a 349-bp segment of the neo gene:upstream primer: 5'-GCATTGCATCAGCCATGATG-3' (SEQ ID NO: I) and downstream primer: 5'-GATGGATTGCACGCAGGTTC-3' (SEQ ID NO:2). The PCR is carried out using well known techniques (e.g., using a GeneAmp kit according to the manufacturer's instructions [Perkin-Elmer]). The DNA present in the reaction is denatured by incubation at 94° C. for 3 min followed by 40 cycles of 94° C. for 1 min, 60° C. for 40 sec and 72° C. for 40 sec followed by a final extension at 72° C. for 5 min. The PCR products may be analyzed by electrophoresis of 10 to 20% of the total reaction on a 2% agarose gel; the 349-bp product may be visualized by staining of the gel with ethidium bromide and exposure of the stained gel to UV light. If the expected PCR product cannot be detected visually, the DNA can be transferred to a solid support (e.g., a nylon membrane) and hybridized with a $^{32}$P-labeled neo probe.

Southern blot analysis of genomic DNA extracted from infected oocytes and/or the resulting embryos, offspring and tissues derived therefrom is employed when information concerning the integration of the viral DNA into the host genome is desired. To examine the number of integration sites present in the host genome, the extracted genomic DNA is typically digested with a restriction enzyme which cuts at least once within the vector sequences. If the enzyme chosen cuts twice within the vector sequences, a band of known (i.e., predictable) size is generated in addition to two fragments of novel length which can be detected using appropriate probes.

V. Detection of Foreign Protein Expression in Transgenic Animals

The present invention also provides transgenic animals that are capable of expressing foreign proteins in their milk, urine and blood. As indicated in Examples 8–10, the transgene is stable, as it is shown to be passed from a transgenic bull to his offspring (See, Example 8). In addition, as shown in Examples 9 and 10, transgenic animals produced according to the present invention express foreign proteins in their body fluids (e.g., milk, blood, and urine). Thus, these data further demonstrate the utility of using the MoMLV LTR as a promoter for driving the constitutive production of foreign proteins in transgenic cattle. It is also contemplated that such a promoter could be used to control expression of proteins that would prevent disease and/or infection in the transgenic animals and their offspring, or be of use in the production of a consistent level of protein expression in a number of different tissues andbody fluids.

For example, it is contemplated that the MoMLV LTR of the present invention will find use in driving expression of antibody to pathogenic organisms, thereby preventing infection and/or disease in transgenic animals created using the methods of the present invention. For example, it is contemplated that antibodies directed against organisms such as *E. coli, Salmonella* ssp., *Streptococcus* ssp., *Staphylococcus* spp., *Mycobacterium* spp., produced by transgenic animals will find use preventing mastitis, scours, and other diseases that are common problems in young animals. It is also contemplated that proteins expressed by transgenic animals produced according to the present invention will find use as bacteriostatic, bactericidal, fungistatic, fungicidal, viricidal, and/or anti-parasitic compositions. Thus, it is contemplated that transgenic animals produced according to the present invention will be resistant to various pathogenic organisms. Furthermore, the milk produced by female transgenic animals would contain substantial antibody levels. It is contemplated that these antibodies will find use in the protection of other animals (e.g., through passive immunization methods).

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); pmol (micromoles); nmol (nanomoles); gm (grams); mg (milligrams); μg (micrograms); μg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); BSA (bovine serum albumin); cDNA (copy or complimentary DNA); CS (calf serum); DNA (deoxyribonucleic acid); ssDNA (single stranded DNA); dsDNA (double stranded DNA); dNTP (deoxyribonucleotide triphosphate); LH (luteinizing hormone); NIH (National Institutes of Health, Besthesda, Md.); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); PBS (phosphate buffered saline); SDS (sodium dodecyl sulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N,N, N',N'-tetraacetic acid); EDTA (ethylenediaminetetraacetic acid); bla (β-lactamase or ampicillin-resistance gene); ORI (plasmid origin of replication); lacI (lac repressor); X-gal (5-bromo-4-chloro-3-indolyl-β-D-galactoside); ATCC (American Type Culture Collection, Rockville, Md.); GIBCO/BRL (GIBCO/BRL, Grand Island, N.Y.); Perkin-Elmer (Perkin-Elmer, Norwalk, Conn.); Abbott (Abbott Laboratories, Diagnostics Division, Abbott Park, Ill. 60064); and Sigma (Sigma Chemical Company, St. Louis, Mo.).

EXAMPLE 1

Generation of Cell Lines Stably Expressing the MoMLV Gag and Pol Proteins

The expression of the fusogenic VSV G protein on the surface of cells results in syncytium formation and cell death. Therefore, in order to produce retroviral particles containing the VSV G protein as the membrane-associated protein a three step approach was taken. First, stable cell lines expressing the Gag and Pol proteins from MoMLV at high levels were generated (e.g., 293GP cells; Example 1). These stable cell lines were then infected using the desired retroviral vector which is derived from an amphotrophic packaging cell (e.g., PA317 cells transfected with the desired retroviral vector; Example 2a). The infected stable cell line which expresses the Gag and Pol proteins produces noninfectious viral particles lacking a membrane-associated protein (e.g., a envelope protein). Third, these infected cell lines are then transiently transfected with a plasmid capable of directing the high level expression of the VSV G protein (Example 2b). The transiently transfected cells produce VSV G-pseudotyped retroviral vectors which can be collected from the cells over a period of 3 to 4 days before the producing cells die as a result of syncytium formation.

The first step in the production of VSV G-pseudotyped retroviral vectors, the generation of stable cell lines expressing the MoMLV Gag and Pol proteins is described below.

The human adenovirus 5-transformed embryonal kidney cell line 293 (ATCC CRL 1573) was cotransfected with the pCMVgag-pol and pFR400 plasmids using a ratio of 10:1 (pCMVgag-pol and pFR400). pCMV gag-pol contains the MoMLV gag and pol genes under the control of the CMV promoter (pCMV gag-pol is available from the ATCQ. pFR400 encodes a mutant dihydrofolate reductase which has a reduced affinity for methotrexate (Simonsen et al., Proc. Natl. Acad. Scl. 80:2495 [1983]).

The plasmid DNA was introduced into the 293 cells using calcium phosphate co-precipitation (Graham and Van der Eb, Virol., 52:456 [1973]). Approximately 5×10$^5$ 293 cells were plated into a 100 mm tissue culture plate the day before the DNA co-precipitate was added. A total of 20 µg of plasmid DNA (18 µg pCMV gag-pol and 2 µg pFR400) was added as a calcium-DNA co-precipitate to each 100 min plate. Stable transformants were selected by growth in DMEM-high glucose medium containing 10% FCS, 0.5 µM methotrexate and 5 µM dipyridimole (i.e., selective medium). Colonies which grew in the selective medium were screened for extracellular reverse transcriptase activity (Goff et al., J. Virol., 38:239 [1981]) and intracellular p30$^{gag}$ expression. p30$^{gag}$ expression was determined by Western blotting using a goat-anti p30 antibody (NCI antiserum 77SO00087). A clone which exhibited stable expression of the retroviral genes in the absence of continued methotrexate selection was selected. This clone was named 293GP (293 gag-pol). The 293GP cell line, a derivative of the human Ad-5-transformed embryonal kidney cell line 293, was grown in DMEM-high glucose medium containing 10% FCS. The 293GP cell line is commercially available from Viagen, Inc., San Diego, Calif.

EXAMPLE 2

Preparation of Pseudotyped Retroviral Vectors Bearing the G Glycoprotein of VSV

In order to produce VSV G protein pseudotyped retrovirus the following steps were taken. First, the 293GP cell line was infected with virus derived from the amphotrophic packaging cell line PA317. The infected cells packaged the retroviral RNA into viral particles which lack a membrane-associated protein (because the 293GP cell line lacks an env gene or other gene encoding a membrane-associated protein). The infected 293GP cells were then transiently transfected with a plasmid encoding the VSV G protein to produce pseudotyped viral particles bearing the VSV G protein.

a) Cell Lines and Plasmids

The amphotropic packaging cell line, PA317 (ATCC CRL 9078) was grown in DMEM-high glucose medium containing 10% FCS. The 293GP cell line was grown in DMEM-high glucose medium containing 10% FCS. The titer of the pseudo-typed virus may be determined using either 208F cells (Quade, Virol., 98:461 [19791], or NIH/3T3 cells (ATCC CRL 1658); 208F and NIH/3T3 cells are grown in DMEM-high glucose medium containing 10% CS.

The plasmid pLZRNL (Xu et al., Virol., 171:331 [1989]) contains the gene encoding E. coli β-galactosidase (LacZ) under the transcriptional control of the LTR of the Moloney murine sarcoma virus (MSV) followed by the gene encoding neomycin phosphotransferase (Neo) under the transcriptional control of the Rous sarcoma virus (RSV) promoter. The plasmid pLSRNL contains the gene encoding the hepatitis B surface antigen gene (HBsAg) under the transcriptional control of the MSV LTR followed by the Neo gene under the control of the RSV promoter (U.S. Pat. No. 5,512,421, the disclosure of which is herein incorporated by reference). The plasmid pHCMV-G contains the VSV G gene under the transcriptional control of the human cytomegalovirus intermediate-early promoter (Yee et al. Meth. Cell Biol., 43:99 [1994]).

b) Production and Titering of Pseudotyped LZRNL Virus pLZRNL DNA was transfected into the amphotropic packaging line PA317 to produced LZRNL virus. The resulting LZRNL virus was then used to infect 293GP cells to produce pseudotyped LZRNL virus bearing the VSV G protein (following transient transfection of the infected 293GP cells with a plasmid encoding the VSV G protein). The procedure for producing pseudotyped LZRNL virus was carried out as described (Yee et al. Meth. Cell Biol., 43:99 [1994]).

Briefly, on day 1, approximately 5×10$^5$ PA317 cells were placed in a 100 mm tissue culture plate. On the following day (day 2), the PA317 cells were transfected with 20 [Ig of PLZRNL plasmid DNA (plasmid DNA was purified using CsCl gradients) using the standard calcium phosphate co-precipitation procedure (Graham and Van der Eb, Virol., 52:456 [1973]). A range of 10 to 40 ug of plasmid DNA may be used. Because 293GP cells may take more than 24 hours to attach firmly to tissue culture plates, the 293GP cells may be placed in 100 mm plates 48 hours prior to transfection. The transfected PA317 cells provide amphotropic LZRNL virus.

On day 3, approximately 1×10$^5$ 293GP cells were placed in a 100 nim tissue culture plate 24 hours prior to the harvest of the amphotropic virus from the transfected PA317 cells. On day 4, culture medium was harvested from the transfected PA317 cells 48 hours after the application of the pLZRNL DNA. The culture medium was filtered through a 0.45 µm filter and polybrene was added to a final concentration of 8 µg/ml. A stock solution of polybrene was prepared by dissolving 0.4 gm hexadimethrine bromide (polybrene; Sigma) in 100 ml sterile water; the stock solution was stored at 4° C. The culture medium containing LZRNL virus (containing polybrene) was used to infect the 293GP cells as follows. The culture medium was removed from the 293GP cells and was replaced with the LZNRL virus containing culture medium. The virus containing medium was allowed to remain on the 293GP cells for 16 hours. Following the 16 hour infection period (on day 5), the medium was removed from the 293GP cells and was replaced with fresh medium containing 400 µg/ml G418 (GIBCO/BRL). The medium was changed every 3 days until G418-resistant colonies appeared two weeks later. Care was taken not to disturb the G418-resistant colonies when the medium was changed as 293GP cells attach rather loosely to tissue culture plates.

The G418-resistant 293 colonies were picked using an automatic pipettor and transferred directly into 24-well plates (i.e., the colonies were not removed from the plates using trypsin). The G418-resistant 293 colonies (as termed "293GP/LZRNL" cells) were screened for the expression of the LacZ gene in order to identify clones which produce high titers of pseudotyped LZRNL virus. Clones in 24-well plates were transferred to 100 mm tissue culture plates and allowed to grow to confluency. Protein extracts are prepared from the confluent plates by washing the cells once with 10 ml PBS (137 mM NaCl, 2.6 mM KCI, 8.1 mM Na2HP04, 1.5 mM KH2PO4). Two ml of 250 mM Tris-HCI, pH 7.8 was added and the cells were scrapped off the plate using a rubber policeman. The cells were then collected by centrifugation at room temperature and resuspended in 100 μl 250 mM Tris-HCl, pH 7.8. The cells were subjected to four rapid freeze/thaw cycles followed by centrifugation at room temperature to remove cell debris. The β-galactosidase activity present in the resulting protein extracts was determined as follows. Five microliters of protein extract was mixed with 500 μl β-gal buffer (50 mM Tris-HCl, pH 7.5, 100 mM NaCl, 10 mM $MgCl_2$) containing 0.75 ONPG (Sigma). The mixtures were incubated at 37° C. until a yellow color appeared. The reactions were stopped by the addition of 500 μl 10 mM EDTA and the optical density of the reactions was determined at 420 nm.

The 293GP/LZRNL clone which generated the highest amount of P-galactosidase activity was then expanded and used subsequently for the production of pseudotyped LZNRL virus as follows. Approximately $1 \times 10^6$ 293GP/LZRNL cells were placed into a 100 mm tissue culture plate. Twenty-four hours later, the cells were transfected with 20 μg of pHCMV-G plasmid DNA using calcium phosphate co-precipitation. Six to eight hours after the calcium-DNA precipitate was applied to the cells, the DNA solution was replaced with fresh culture medium (lacking G418). Longer transfection times (overnight) have been found to result in the detachment of the majority of the 293GP/LZRNL cells from the plate and are therefore avoided. The transfected 293GP/LZRNL cells produce pseudotyped LZRNL virus.

The pseudotyped LZRNL virus generated from the transfected 293GP/LZRNL cells can be collected at least once a day between 24 and 96 hr after transfection. The highest virus titer was generated approximately 48 to 72 hr after initial pHCMV-G transfection. While syncytium formation became visible about 48 hr after transfection the majority of the transfected cells, the cells continued to generate pseudotyped virus for at least an additional 48 hr as long as the cells remained attached to the tissue culture plate. The collected culture medium containing the VSV G-pseudotyped LZRNL virus was pooled, filtered through a 0.45 μm filter and stored at −70° C.

The titer of the VSV G-pseudotyped LZRNL virus was then determined as follows. $5 \times 10^5$ rat 208F fibroblasts or NIH 3T3 cells were plated in a 100 min culture plate. Twenty-fours hours after plating, the cells were infected with serial dilutions of the LZRNL virus containing culture medium in the presence of 8 μg/ml polybrene. Sixteen hours after infection with virus, the medium was replaced with fresh medium containing 400 μg/ml G418 and selection was continued for 14 days until G418-resistant colonies became visible. Viral titers were typically about 0.5 to $5.0 \times 10^6$ colony forming units (cfu)/ml. The titer of the virus stock could be concentrated to a titer of greater than 109 cfu/ml as described below.

EXAMPLE 3

Concentration of Pseudotyped Retroviral Vectors

The VSV G-pseudotyped LZRNL virus was concentrated to a high titer by two cycles of ultracentrifugation. The frozen culture medium collected as described in Example 2 which contained pseudotyped LZRNL virus was thawed in a 37° C. water bath and was then transferred to ultraclear centrifuge tubes (14×89 min; Beckman, Palo Alto, Calif.) which had been previously sterilized by exposing the tubes to UV light in a laminar flow hood overnight. The virus was sedimented in a SW41 rotor (Beckman) at 50,000×g (25,000 rpm) at 4° C. for 90 min. The culture medium was then removed from the tubes in a laminar flow hood and the tubes were well drained. The virus pellet was resuspended to 0.5 to 1% of the original volume of culture medium in either TNE (50 mM Tris-HCl, pH 7.8; 130 mM NaCl; I mM EDTA) or 0.1× Hank's balanced salt solution (1× Hank's balanced salt solution contains 1.3 mM $CaCl_2$, 5 mM KCl, 0.3 mM $KH_2PO_4$, 0.5 mM $MgCl_2.6H_2$), 0.4 mM $MgSO_4.7H_2O$, 138 mM NaCl, 4 mM $NaHCO_3$, 0.3 mM $NaH_2PO_4.H_2O$; 0.1× Hank's is made by mixing 1 parts 1× Hank's with 9 parts PBS]. The resuspended virus pellet was incubated overnight at 4° C. without swirling. The virus pellet could be dispersed with gentle pipetting after the overnight incubation without significant loss of infectious virus. The titer of the virus stock was routinely increase 100- to 300-fold after one round of ultracentrifugation. The efficiency of recovery of infectious virus varied between 30 and 100%.

The virus stock was then subjected to low speed centrifugation in a microfuge for 5 min at 4° C. to remove any visible cell debris or aggregated virions that were not resuspended under the above conditions (if the virus stock is not to be used for injection into oocytes or embryos, this centrifugation step may be omitted).

The virus stock was then subjected to another round of ultracentrifugation to concentrate the virus stock further. The resuspended virus from the first round of centrifugation was pooled and pelleted by a second round of ultracentrifugation which was performed as described above. Viral titers were increased approximately 2000-fold after the second round of ultracentrifugation (titers of the pseudotyped LZRNL virus were typically greater than or equal to $1 \times 10^9$ cfu/ml after the second round of ultracentrifugation).

The titers of the pre- and post-centrifugation fluids were determined by infection of 208F (NIH 3T3 or Mac-T cells can also be employed) followed by selection of G418-resistant colonies as described above in Example 2. The concentrated viral stock was stable (i.e., did not lose infectivity) when stored at 4° C. for several weeks.

EXAMPLE 4

Preparation of Pseudotyped Retrovirus For Infection of Oocytes and Embryos

The concentrated pseudotyped retrovirus were resuspended in 0.1× HBS (2.5 mM HEPES, pH 7.12, 14 mM NaCl, 75 μM $Na_2HPO_4.H_2O$) and 18 μl aliquots were placed in 0.5 ml vials (Eppendorf) and stored at −80° C. until used. The titer of the concentrated vector was determined by diluting 1 μl of the concentrated virus $10^{-7}$- or $10^{-8}$-fold with 0.1× HBS. The diluted virus solution was then used to infect 208F and Mac-T cells and viral titers were determined as described in Example 2.

Prior to infection of oocytes or embryos (by microinjection), 1 μl of polybrene (25 ng/μl; the working solution of polybrene was generated by diluting a stock solution having a concentration of 1 mg/ml [in sterile $H_2O$], in 0.1 HBS, pH 7.12) was mixed with 4 μl of concentrated virus to yield a solution containing $10^3$–$10^4$ cfu/μl and 8 μg/ml polybrene. This solution was loaded into the injection needle (tip having an internal diameter of approximately 2–4 μm) for injection into the perivitelline space of gametes (pre-maturation oocytes, matured oocytes) or one cell stage zygotes (early stage embryo). An Eppendorf Transjector 5246 was used for all microinjections.

EXAMPLE 5

Preparation and Microinjection of Gametes and Zygotes

Gametes (pre-maturation and pre-fertilization oocytes) and zygotes (fertilized oocytes) were prepared and microinjected with retroviral stocks as described below.

a) Solutions

Tyrodes-Lactate with HEPES (TL-HEPES): 114 mM NaCl, 3.2 mM KCl, 2.0 mM $NaHCO_3$, 0.4 mM $Na_2H_2PO_4.H_2O$, 10 mM Na-lactate, 2 mM $CaCl_2.2H_2O$, 0.5 mM $MgCl.6H_2O$, 10 mM HEPES, 100 IU/ml penicillin, 50 µg/ml phenol red, I mg/ml BSA fraction V, 0.2 mM pyruvate and 25 µg/ml gentamycin.

Maturation Medium: TC-199 medium (GIBCO) containing 10% FCS, 0.2 mM pyruvate, 5 µg/ml NIH o-LH (NIH), 25 µg/ml gentamycin and lpg/ml estradiol-17β.

Sperm-Tyrodes-Lactate (Sperm-TL): 100 mM NaCl, 3.2 mM KCl, 25 mM $NaHCO_3$, 0.29 mM $Na_2H_2PO4.H_2O$, 21.6 mM Na-lactate, 2.1 mM $CaCl_2.2H_2O$, 0.4 mM $MgCl_2.6H_2O$, 10 mM HEPES, 50 µg/ml phenol red, 6 mg/ml BSA fraction V, 1.0 mM pyruvate and 25 µg/ml gentamycin.

Fertilization Medium: 114 mM NaCl, 3.2 mM KCl, 25 mM $NaHCO_3$, 0.4 mM $Na_2H_2PO_4.H_2O$, 10 mM Na-lactate, 2 mM $CaCl_2.2H_2O$, 0.5 mM $MgCl_2.6H_2O$, 100 IU/ml penicillin, 50 µg/ml phenol red, 6 mg/ml BSA fatty acid free, 0.2 mM pyruvate and 25 µg/ml gentamycin.

PHE: 1 mM hypotaurine, 2 mM penicillamine and 250 µM epinephrine.

Embryo Incubation+Amino Acids (EIAA): 114 µM NaCl, 3.2 µM KCl, 25 µM $NaHCO_3$, 1.6 µg/ml L(+)-lactate, 10.7 µg/ml L-glutamine, 300 µg/ml BSA fatty acid free, 0.275 µg/ml pyruvate, 25 µg/ml gentamycin, 10 µl of 100× MEM amino acids stock (M7145, Sigma) per µl and 20 µl of 50× BME amino acids stock (B6766, Sigma) per ml.

0.1× HBS: 2.5 mM HEPES (pH 7.12), 14 mM NaCl and 75 µM $Na_2HPO_4.H_2O$.

b) Preparation, Injection, Maturation and Fertilization of Pre-Maturation Oocytes Oocytes were aspirated from small antral follicles on ovaries from dairy cattle obtained from a slaughterhouse. Freshly aspirated oocytes at the germinal vesicle (GV) stage, meiosis arrested, with the cumulus mass attached were selected (i.e., pre-maturation oocytes). The oocytes were then washed twice in freshly prepared TL-HEPES and transferred into a 100 µl drop of TL-HEPES for microinjection.

Concentrated retroviral particles (prepared as described in Example 3) were resuspended in 0.1× HBS, mixed with polybrene and loaded into the injection needle as described in Example 4. Approximately 10 pl of the virus solution was then injected into the perivitelline space of pre-maturation oocytes.

Following injection, the pre-maturation oocytes were washed twice in fresh TL-HEPES and transferred into maturation medium (10 oocytes in 50 µl). The pre-maturation oocytes were then incubated in Maturation Medium for 24 hours at 37° C. which permits the oocytes to mature to the metaphase 11 stage. The matured oocytes were then washed twice in Sperm-TL and 10 oocytes were then transferred into 44 µl of Fertilization Medium. The mature oocytes (10 oocytes/44 µl Fertilization Medium) were then fertilized by the addition of 2 µl of sperm at a concentration of $2.5×10^7$/ml, 2 µl of PHE and 2 µl of heparin (fertilization mixture). Sperm was prepared by discontinuous percoll gradient separation of frozen-thawed semen as described (Kim et al., Mot. Reprod. Develop., 35:105 [19931). Briefly, percoll gradients were formed by placing 2 ml of each of 90% and 45% percoll in a 15 ml conical tube. Frozen-thawed semen was layered on top of the gradient and the tubes were centrifuged for 10 minutes at 700×g. Motile sperm were collected from the bottom of the tube.

The oocytes were incubated for 16 to 24 hours at 37° C. in the fertilization mixture. Following fertilization, the cumulus cells were removed by vortexing the cells (one cell stage zygotes, Pronucleus Stage) for 3 minutes to produce "nude" oocytes. The nude oocytes were then washed twice in embryo culture medium (ElAA) and 20 to 25 zygotes were then cultured in 50 µl drop of ElAA (without serum until Day 4 at which time the zygotes were placed in EIAA containing 10% serum) until the desired developmental stage was reached: approximately 48 hours or Day 2 (Day 0 is the day when the matured oocytes are co-cultured with sperm) for morula stage (8 cell stage) or Day 6–7 for blastocyst stage. Embryos at the morula stage were analyzed for expression of β-galactosidase as described in Example 6. Embryos derived from injected pre-maturation oocytes were also analyzed for β-galactosidase expression at the 2 cell, 4 cell, and blastocyst stage and all developmental stages examined were positive.

c) Preparation, Injection and Fertilization of Pre-Fertilization Oocytes

Pre-maturation oocytes were harvested, washed twice with TL-HEPES as described above. The oocytes were then cultured in Maturation Medium (10 oocytes per 50 µl medium) for 16 to 20 hours to produce pre-fertilization oocytes (Metaphase 11 Stage). The pre-fertilization or matured oocytes were then vortexed for 3 minutes to remove the cumulus cells to produce nude oocytes. The nude oocytes were washed twice in TL-HEPES and then transferred into a 100 µl drop of TL-HEPES for microinjection. Microinjection was conducted as described above.

Following microinjection, the pre-fertilization oocytes were washed twice with TL-HEPES and then placed in Maturation Medium until fertilization. Fertilization was conducted as described above. Following fertilization, the zygotes were then washed twice in ElAA and 20 to 25 zygotes were then cultured per 50 µl drop of ElAA until the desired developmental stage was reached. The embryos were then examined for P-galactosidase expression (Ex. 6) or transferred to recipient cows (Ex. 7).

d) Preparation and Injection of One-Cell Stage Zygotes

Matured oocytes (Metaphase 11 stage) were generated as described above. The matured oocytes were then co-cultured in the presence of sperm for 16 to 20 hours as described above to generate zygotes at the pronucleus stage. Zygotes at the pronucleus stage were vortexed for 3 minutes to remove the cumulus cell layer prior to microinjection. Microinjection of retrovirus was conducted as described above. Following microinjection, the zygotes were washed four times in EIAA and then placed in an EIAA culture drop (25 zygotes per 50 µl drop of EIAA). The zygotes were cultured in EIAA (20 to 25 zygote per 50 µl drop of EIAA) until the desired developmental stage was reached. The embryos were then examined for β-galactosidase expression (Ex. 6) or transferred to recipient cows (Ex. 7).

EXAMPLE 6

Injection of Pseudotyped Retrovirus into the Perivitelline Space of Maturing Bovine Oocytes Results in the Efficient Transfer of Vector Sequences Oocytes and one-cell zygotes which had been microirijected with pseudotyped LZRNL virus and cultured in vitro were examined for expression of vector sequences by staining for β-galactosidase activity when the embryos had reached the morula stage. β-galactosidase activity was examined as follows. Embryos were washed twice in PBS then fixed in 0.5% glutaraldehyde in PBS containing 2 mM $MgCl_2$ for 40 min. at 4° C. The fixed embryos were then washed three times with PBS containing 2 mM $MgCl_2$ and then incubated at 37° C. overnight in X-gal solution (20 mM $K_3Fe(CN)_6$, 20 mM $K_4Fe(CN)6.H_2O$, 2 mM $MgCl_2$ and 1 mg/ml X-gal). The presence of a blue precipitate indicates expression of β-galactosidase activity. The results are shown in Table I below.

TABLE 1

| Stage at Injection | Stage at Analysis | % Positive For β-galactosidase Expression |
|---|---|---|
| Pre-Fertilization Oocyte (injected 20–24 hrs after exposure to Maturation Medium) | Morula | 47 (80/172)[a] |
| Pronuclei Stage (injected 18–20 hrs after exposure to sperm) | Morula | 25 (20/80) |
| One-Cell Zygote | Morula | 25 (20/80) |

[a]Number positive/number injected.

From the results shown in Table 1, it is clear that infection of pre-fertilization oocytes and zygotes using the methods of the present invention results in the transfer and expression of retrovirally encoded nucleic acid. While not limiting the present invention to any particular theory, it is currently believed that only half of the daughter cells from an initial founder cell infected with a retrovirus will contain the provirus because the retroviral provirus integrates into post-replication host DNA (Hajihosseini et al., EMBO J., 12:4969 [1993]). Therefore, the finding that 47% of the injected pre-fertilization oocytes are positive for galactosidase expression suggests that 100% of these injected oocytes were infected with the recombinant retrovirus. Therefore, the methods of the present invention provide an efficiency of generating transgenic embryos which is superior to existing methods.

EXAMPLE 7

Generation of Transgenic Cows Containing Integrated Retroviral Nucleic Acid Sequences Embryos derived from infected pre-fertilization oocytes and early zygotes were transferred into recipient cows which were allowed to progress to term as described below.

a) Treatment of Embryos Derived from Infected Oocytes and Zygotes

Pre-fertilization oocytes (infected about 17 hours after exposure to Maturation Medium) and early stage zygotes (≧8 cell stage) were prepared and infected as described in Example 5 with the exceptions that 1) the VSV-G-pseudotyped virus used was the LSRNL virus which was prepared as described for the LZRNL virus in Ex. 2, and 2) at day 4 post-fertilization, embryos derived from injected pre-fertilization oocytes and zygotes were placed in freshly prepared EIAA medium containing 10% FCS and allowed to develop in vitro until transfer into recipient cows. Embryos at Day 7 were transferred into recipient females which were prepared as described below.

b) Preparation of Recipient Cows and Embryo Transfer

Recipient cows were synchronized by injecting 100 µg of gonadotropin-releasing hormone (GnRH; Sanofi Winthrop Pharmaceutical Inc., New York, N.Y.) (Day 0). Seven days later, the recipients were injected with 25 mg of PGF2α (Upjohn Co., Kalamazoo, Mich.). Thirty to 48-hours after injection of PGF2α, a second injection of 100 µg of GnRH was given. Ovulation occurs about 24–32 hours post injection. Seven days after ovulation occurred, embryos derived from infected oocytes and zygotes (Day 7 embryos) were then transferred nonsurgically to the uteri the recipient cows. Two embryos were transferred into each recipient (it is expected that only one calf will be born from the transfer of two embryos into a single recipient).

A total of 20 embryos were transferred into recipients on three separate days. In the first transfer 8 embryos derived from infected pre-fertilization oocytes were transferred into 4 recipients; four calves were born to these recipients and all four were found to be positive for the presence of vector proviral DNA (i.e., 100% were transgenic). In the second transfer, 8 embryos derived from post-fertilization zygotes were transferred into 4 recipients; 2 calves were born to these recipients and one of these animals was found to be transgenic (in the second transfer, one pregnancy was lost in the first month and another pregnancy comprising twins was lost in the eighth month; neither embryo from the 8 month pregnancy was transgenic). In the third transfer 4 embryos derived from infected zygotes (infected at the 4–8 cell stage) were transferred into 2 recipients; 3 calves were born to these recipients and none were transgenic.

The nine calves appeared healthy at birth and continue to appear healthy at the age of 6 months. Following the birth of offspring derived from the injected oocytes and zygotes, the offspring were examined by Southern blot and PCR analyses to determine whether they contained the retroviral transgenes and whether they exhibited somatic cell mosaicism. Skin tissue and white blood cells (buffy coat) was collected from the calves. Genomic DNA was extracted using standard techniques. Briefly, the tissue samples were digested with 50 µg/ml proteinase K (GIBCO) at 55° C. The samples were then extracted sequentially twice with an equal volume of phenol, once with phenol: chloroform (1:1) and once with chloroform. The DNA present in the aqueous layer was then precipitated by the addition of 2 volumes of isopropanol. The DNA was collected by centrifugation and the DNA pellet was resuspended in TE buffer (10 mM Tris-Cl, 1 mM EDTA, pH 8.0) and the concentration was determined spectrophotometrically. The DNA was then analyzed by Southern blotting and PCR analysis. The results are shown in FIGS. 2 and 3.

Figure 1:
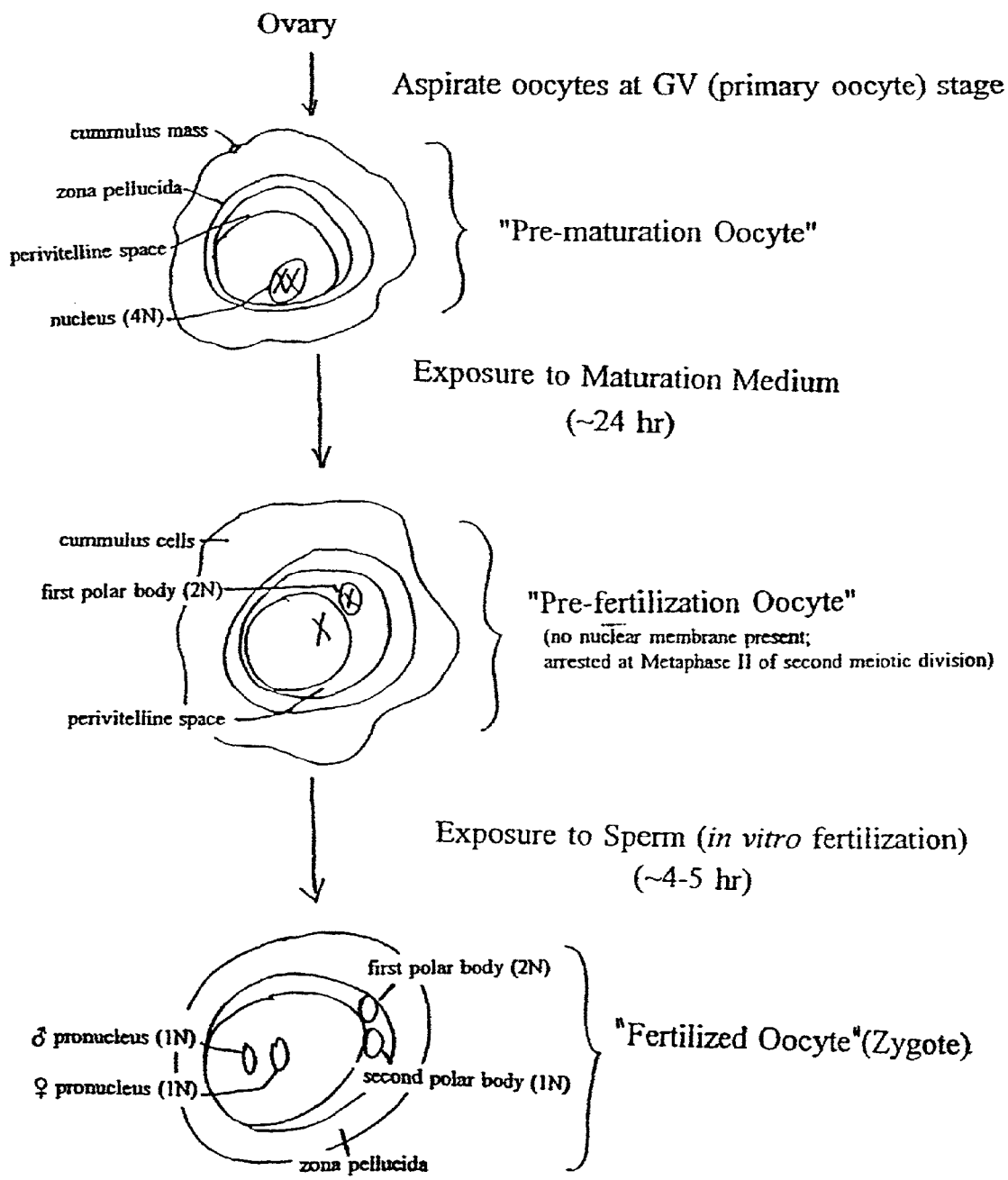
FIG. 1 provides a schematic showing the production of pre-maturation oocytes, pre-fertilization oocytes and fertilized oocytes (zygotes).
Figure 2:
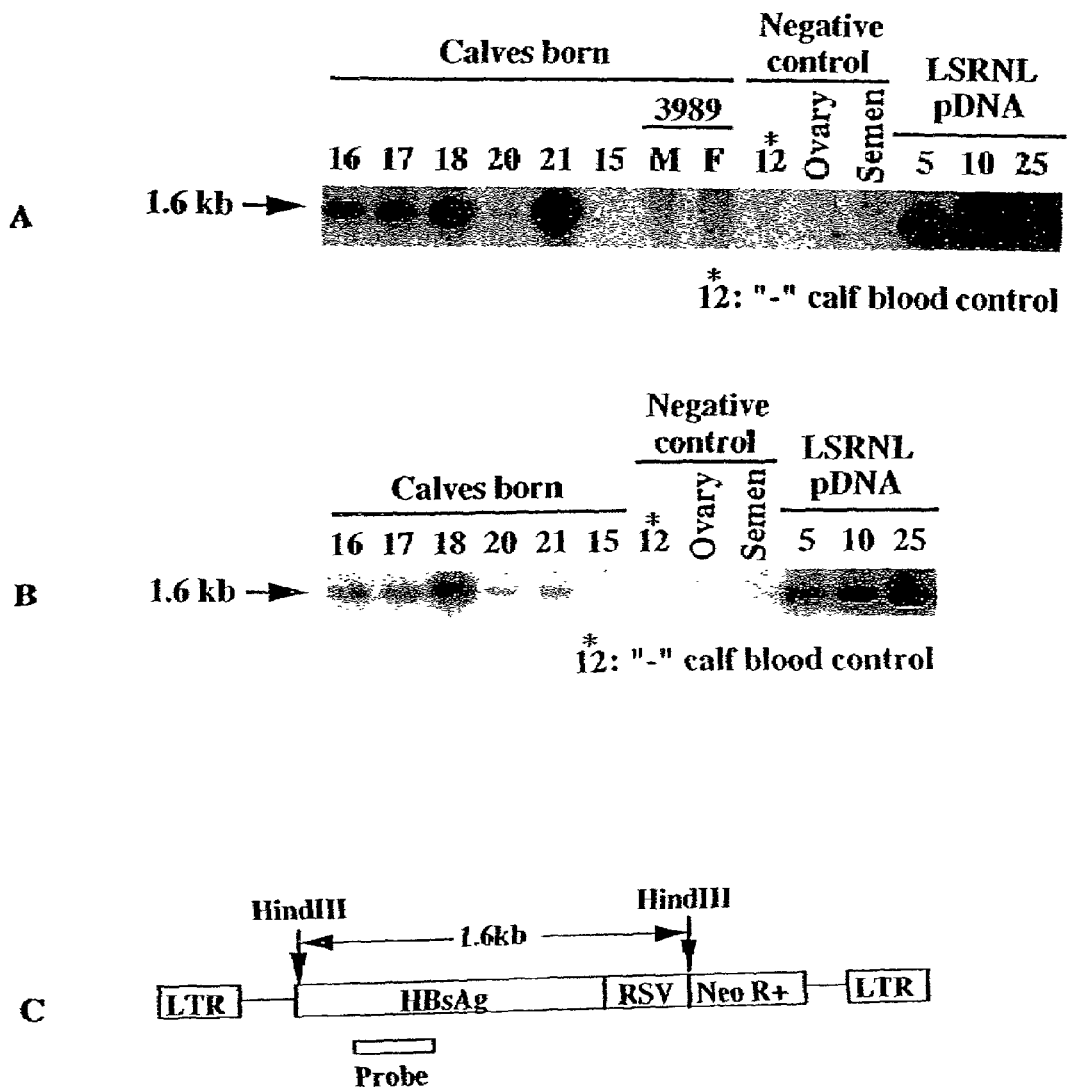
FIG. 2 shows an autoradiogram of a Southern blot of genomic DNA isolated from the skin (A) and blood (B) of calves derived from pre-fertilization oocytes and zygotes which were injected with pseudotyped LSRNL retrovirus.
Figure 3:
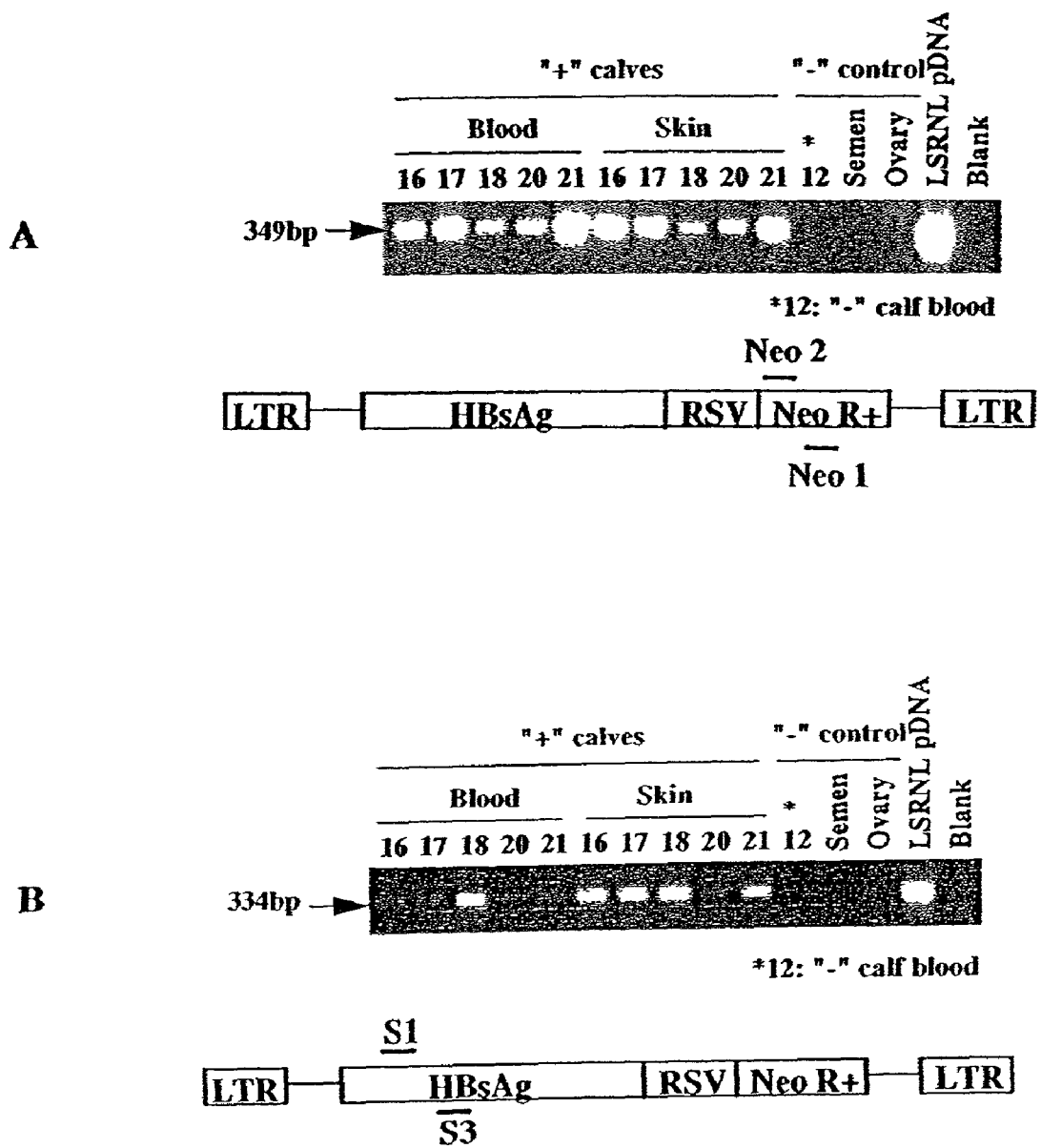
FIG. 3 shows an ethidium bromide stained agarose gel containing electrophoresed PCR products which were amplified using neo gene primers (A) or HBsAg primers (B)

FIG. 2 shows an autoradiography of a Southern blot of genomic DNA isolated from the skin (FIG. 2A) and blood (FIG. 2B) of the six calves derived from either pre-fertilization oocytes infected with VSV G-pseudotyped LSRNL virus at about 17 hours after exposure to Maturation Medium (calves numbered 17, 18, 20 and 21) or one cell zygotes infected at about 12 hrs post-fertilization (calves numbered 15 and 16). The calf DNA was digested with HindIII which cuts the pLSRNL vector twice to generate a 1.6 kb fragment (FIG. 2C). HindIII-digested DNA from the blood (lane labelled *12 derived from a random, nontransgenic calf), ovary and semen of nontransgenic cows (derived random adult females and males) were also included. Lanes labeled "3989 M and F" represent DNA derived from two late term embryos that were born one month prematurely (these calves were generated from injected fertilized eggs and both are nontransgenic). Lanes labelled "LSRNL pDNA" contain HindIII-digested pLSRNL plasmid DNA and provide controls for the quantitation of the copy number of the integrated proviruses in the offspring (DNA equivalent to 5, 10 or 25 copies of LSRNL were applied in these lanes).

Approximately 10 µg of the HindIII-digested DNAs were electrophoresed on 0.8% agarose gels, and blotted onto a nylon membrane. The membrane was hybridized with a $^{32}$P labelled probe which hybridizes to the HBsAg gene present in the pLZRNL vector (FIG. 2C). The HBsAG probe was generated by PCR amplification of pLSRNL plasmid DNA using the upstream primer S-1 (5'-GGCTATCGCTGGAT-GTGTCT-3'; [SEQ ID NO:3]) and the downstream primer S-3 (5'-ACTGAACAAATGGCACTAGT-3'-[SEQ ID NO:4]). The PCR-generated probe (334 bp) was labeled using a Rediprime kit (Amersham, Arlington Heights, Ill.) according to the manufacturer's instructions. The autoradiographs shown in FIG. 2 were generated by exposure of the blots to X-ray film for 3 weeks at −80° C.

The results shown in FIG. 2 demonstrates that calves 16, 17, 18, 20 and 21 contained retroviral vector DNA in both the skin (FIG. 2A) and blood (FIG. 2B). As blood cells (buffy coat) are derived from the mesoderm and skin cells are derived from the ectoderm, these results show that the transgenic animals do not display somatic cell mosaicism. Southern blotting analysis has shown that the majority (i.e., 7/9) of the transgenic calves contain a single copy of the proviral sequence; a few (i.e., 2/9) animals appear to contain two copies of the integrated proviral sequence. These results further demonstrate that retroviral infection of both pre-fertilization oocytes and early stage zygotes was successful in integrating the viral sequences into the genome of the resulting transgenic animals.

In order to confirm the presence of integrated retroviral sequences in the genome of the transgenic animals' somatic cells, PCR analysis (FIG. 3) was performed using genomic DNA isolated from the five transgenic calves which were determined by Southern blot analysis to be transgenic for the retroviral sequences. FIG. 3 shows the results of the PCR analysis following amplification of two different regions (i.e., the neo gene and the HbsAg gene) of the LZRNL retroviral genome which was injected into the oocytes. Genomic DNA from the skin and blood of each of the five transgenic calves was amplified using the upstream and downstream primers (SEQ ID NOS:1 and 2 and NOS:3 and 4; described supra) for the neo (FIG. 3A) and HBsAg (FIG. 3B) genes, respectively. The PCRs were conducted using the following thermocycling conditions: 94° C. (4 min); (94° C. [2 min]; 50° C. [2 min]; 72° C. [2 min])$_{30\ cycles}$; 72° C. (10 min). Amplification yielded the expected size of amplified sequence with the neo (349 bp) and HBsAg (334 bp) primers in both the blood and skin of each of the five transgenic calves. Genomic DNA isolated from the blood of non-transcyenic calves as well as from semen and ovary of non-transgenic cattle were used as negative controls in the PCRs. PLSRNL DNA was used as the positive control.

These data demonstrate that the infection of pre-fertilization oocytes results in the efficient transfer of retroviral vector DNA (100% or 4 transgenic calves/4 calves born from embryos derived from infected pre-fertilization oocytes). In addition to providing a means for efficiently generating transgenic animals, the methods of the present invention provide a means for generating transgenic animals which do not display somatic cell mosaicism. Further, these methods permit the production of transgenic animals which contain a single copy of the transgene.

In order to confirm germ line transmission of the integrated viral sequences, the transgenic offspring are bred with non-transgenic cattle and the presence of the viral sequences (i.e., the transgene) determined using Southern blot analysis or PCR amplification as described above. Animals which are heterozygous or homozygous for the transgene are produced using methods well known to the art (e.g., interbreeding of animals heterozygous for the transgene).

EXAMPLE 8

Detection of the HBsAg Transgene in the Sperm of Transgenic Bulls

Semen was collected from two transgenic bulls, #16 and #21. DNA was isolated from the semen samples using methods known in the art. PCR was then conducted on the sample DNA, using the primers SI and S3, as described below. The PCR results indicated that both bulls had the transgene in their sperm.

These results demonstrated that transgenic bulls produced either by perivitelline space injection of an unfertilized oocyte (#21) or by perivitelline space injection of a fertilized zygote (#16) have the transgene present in their sperm, and are thus capable of passing the transgene on to their offspring. Indeed, as described in Example 9 below, bull #16 has produced two live transgenic offspring.

EXAMPLE 9

Confirmation of Transgene Stability

To confirm the transgene stability of a transgenic bull produced as described in the previous Examples, and to determine whether the gene was behaving in a normal Mendelian fashion, a transgenic bull (designated as #16) produced through one-cell zygotic injection, was naturally mated with a non-transgenic cow. This mating resulted in the production of twill calves, one female (designated as #42) and one male (designated as #43). Blood and skin samples were taken from each of the calves, and their DNA was isolated using methods known in the art (See e.g., Hogan et al., Manipulating the Mouse Embryo: A Laboratory Manual, Cold Spring Harbor Laboratory, Cold Spring Harbor, N.Y. [1986]). PCR was performed on these DNA samples, using the methods described in Example 7, above. Two sets of primers were used to analyze both the blood and skin samples. One set of primers ("Neo1" and "Neo2") was used to detect the neomycin resistance gene in the LSRNL vector. The location and description of these primers is shown in FIG. 3A. The second set of primers (S1 and S3) were used to detect a portion of the Hepatitis B surface antigen (HbsAg) gene in the LSRNL vector. The location and description of these primers is shown in FIG. 3B. Both the skin and blood samples from these calves were positive for the LSRNL transgene, indicating that the gene can be transmitted from an original transgenic bull created by one-cell zygotic injection, to his offspring. FIG. 4 shows the results of PCR screening of skin samples from these calves. In this gel, the control animal is indicated as #12, while the offspring are indicated as #42 and #43, as described above. Lane one contains DNA size standards, and lanes 2–4 contain the DNA samples analyzed using the neo PCR primers, while lanes 5–7 contain the same DNA samples analyzed using the HBsAg PCR primers. The correct size for the neo band is 349 base pairs, while the correct size for the HBsAg band is slightly smaller, at 334 base pairs.

These data demonstrate that transgenic animals can be successfully created by perivitelline space injection of a one-cell zygote with a pseudotyped replication-defective retrovirus. In addition, these data also demonstrate that the incorporated transgene is passed on the offspring of the transgenic animal.

EXAMPLE 10

Production of HBsAg in Milk of Transgenic Cows

In this experiment, female founder transgenic heifers (designated as #17 and #18), were artificially induced to lactate at 22 months of age, using a protocol described by Dommer (Dommer, "Artificial Induction of Lactation in Nulligravida Heifers," MS Thesis, University of Wisconsin, Madison, 1996; and Dommer and Bremel, J. Dairy Sci., 79 (Suppl. 1):146 [1996]). After induction of lactation and the subsequent secretion of milk, the milk was assayed for the presence of HBsAg.

Milk samples were collected from #17 and #918, and five control heifers that had also been artificially induced to lactate using the same protocol and at the same time as #17 and #18. Whole milk samples were analyzed using the AUSZYME® Monoclonal Antibody Assay (Abbott), for the detection of HbsAg.

The milk samples collected from #17 and #18 tested positive for HBsAg. The milk samples from the five control heifers were all negative for the antigen. The estimated level of HBsAg production, based on the AUSZYME® kit and its positive control, as well as a dilution series of the milk samples, was found to be 200 ng HBsAg/ml milk, for #17, and 700 ng HBsAg/ml milk, for #18.

These data clearly demonstrate that transgenic animals produced by perivitelline space injection of an unfertilized oocyte are capable of producing substantial levels of foreign proteins in their milk. In addition, these experiments also demonstrate the utility of using the MoMLV LTR as a promoter for driving the production of foreign proteins in the milk of transgenic cattle, as this promoter was shown to be capable of causing the production of HBsAg in the milk of these transgenic animals. In addition, the expression of an exonless construct (i.e., with the LTR of the present invention) indicates that the LTR is also functioning as an enhancer. Furthermore, these data clearly show that the expression system of the present invention is capable of preferential mammary expression, even tliougli the MoMLV LTR is not a "mammary-specific" promoter.

EXAMPLE 11

Presence HBsAg in the Serum and Urine of Transgenic Cattle

In addition to milk samples, blood and urine samples were also collected from the two female founder transgenic heifers #17 and #18. The serum was separated from the whole blood using methods known in the art (i.e., centrifugation). The urine and serum samples were assayed for the presence of HBsAg using the AUSZYME® system, as per the kit manufacturer's instructions. The urine and serum of #17 and #18 all tested positive for the presence of HBsAg, while the urine and serum samples from the control animals all tested negative. Based on this test system, the estimated level of HBsAg production for #17 was 2.58 ng HBsAg/ml of serum, and 0.64 ng HBsAg/ml of urine. For #18, the values were 0.64 ng HBsAg/ml of serum, and 0.97 ng HBsAg/ml of urine.

These data demonstrate that transgenic animals produced by perivitelline space injection of an unfertilized oocyte are capable of producing substantial levels of foreign proteins in their serum and urine. These data further demonstrate the utility of using the MoMLV LTR as a promoter for driving the constitutive production of foreign proteins in transgenic cattle, as this promoter was shown in these experiments to cause the production of HBsAg in milk, serum, and urine of transgenic cattle. As used herein, the term "constitutive" refers to a relatively low level of expression throughout the animal's body. In contrast, the term "preferentially expressed" indicates that a relatively high level of expression is achieved in certain tissues or body fluids, as compared to other tissues and fluids. For example, in preferred embodiments of the present invention, foreign proteins of interest are preferentially expressed in such fluids as milk.

It is contemplated that such a promoter could be used to control expression of proteins that would prevent disease and/or infection in the transgenic animals and their offspring, or be of use in the production of a consistent level of protein expression in a number of different tissues and body fluids.

From the above it is clear that the invention provides improved methods and compositions for the production of transgenic non-human animals. The methods of the present invention provide for the production of transgenic non-human animals with improved efficiency and a reduced incidence of generating animals which are mosaic for the presence of the transgene.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, transgenic animals, or related fields are intended to be within the scope of the following claims.

The invention claimed is:

1. A method for introducing a polynucleotide contained within the genome of a recombinant retrovirus into the genome of a non-human mammalian zygote, comprising:

a) providing a plurality of non-human mammalian zygotes, each having a plasma membrane and a zona pellucida, said plasma membrane and said zona pellucida defining a perivitelline space;

b) providing an aqueous solution, which has been rendered cell-free by ultracentrifugation, wherein said cell-free aqueous solution comprises a polynucleotide contained within the genome of a recombinant retrovirus;

c) introducing said solution comprising said polynucleotide contained within the genome into said perivitelline space by injection through a needle, under conditions which permit the integration of said polynucleotide contained within the genome of a recombinant retrovirus into the genome of said zygotes, such that said polynucleotide is stably maintained, thereby integrating the polynucleotide into the genome of at least twenty percent of said zygotes; and d) culturing said zygotes which have integrated the polynucleotide in their genomes.

2. The method of claim 1, wherein said polynucleotide contained within the genome of a recombinant retrovirus encodes a protein of interest.

3. The method of claim 2, further comprising the step of selecting a cultured zygote from said zygotes which have integrated the polynucleotide in their genomes and transferring said zygote into a non-human mammalian recipient that is hormonally synchronized to simulate early pregnancy, thereby giving a transferred embryo.

4. The method of claim 3, further comprising the step of allowing said transferred embryo to develop to term.

5. The method of claim 4, further comprising the step of identifying at least one transgenic offspring.

6. The method of claim 5, wherein said transgenic offspring expresses said protein of interest.

7. The method of claim 1, wherein said recombinant retrovirus comprises a Moloney murine leukemia virus long terminal repeat.

8. The method of claim 1, wherein said recombinant retrovirus comprises a heterologous membrane-associated protein.

9. The method of claim 8, wherein said heterologous membrane-associated protein is a G glycoprotein selected from a virus within the family Rhabdoviridae.

10. The method of claim 9, wherein said G glycoprotein is selected from the group consisting of the G glycoprotein of vesicular stomatitis virus, Piry virus, Chandipura virus, Spring viremia of carp virus, Rabies virus, and Mokola virus.

11. A method for introducing a polynucleotide contained within the genome of a recombinant pseudotyped retrovirus into the genome of a non-human mammalian zygote, comprising:

a) providing a non-human mammalian zygote having a plasma membrane and a zona pellucida, said plasma membrane and said zona pellucida defining a perivitelline space;

b) providing an aqueous solution, which has been rendered cell-free by ultracentrifugation, wherein said cell-free aqueous solution comprises a polynucleotide contained within the genome of a recombinant pseudotyped retrovirus; and c) introducing said solution comprising said polynucleotide contained within the recombinant retrovirus into said perivitelline space by injection through a needle, under conditions which permit the integration of said polynucleotide contained within the pseudotyped retrovirus into the genome of said zygote, such that said polynucleotide is stably maintained.

12. The method of claim 11, wherein the introduction of said polynucleotide contained within the genome of a pseudotyped retrovirus results in integration of the polynucleotide in at least twenty percent of the zygotes into which the polynucleotide is introduced.

13. The method of claim 11, wherein said polynucleotide contained within the genome of a pseudotyped retrovirus encodes a protein of interest.

14. The method of claim 13, further comprising the step of transferring said zygote into a non-human mammalian recipient that is hormonally synchronized to simulate early pregnancy, thereby giving a transferred embryo.

15. The method of claim 14, further comprising the step of allowing said transferred embryo to develop to term.

16. The method of claim 15, further comprising the step of identifying at least one transgenic offspring.

17. The method of claim 11, wherein said pseudotyped retrovirus comprises a Moloney murine leukemia virus long terminal repeat.

18. The method of claim 16, wherein said transgenic offspring expresses said protein of interest.

19. The method of claim 11, wherein said pseudotyped retrovirus comprises a heterologous membrane-associated protein.

20. The method of claim 19, wherein said heterologous membrane-associated protein is a G glycoprotein selected from a virus within the family Rhabdoviridae.

21. The method of claim 20, wherein said G glycoprotein is selected from the group consisting of the G glycoprotein of vesicular stomatitis virus, Piry virus, Chandipura virus, Spring viremia of carp virus, Rabies virus, and Mokola virus.

* * * * *